(12) United States Patent
Shu

(10) Patent No.: US 6,475,987 B1
(45) Date of Patent: Nov. 5, 2002

(54) TALL-1 RECEPTOR HOMOLOGUES

(75) Inventor: Hong-Bing Shu, Denver, CO (US)

(73) Assignee: National Jewish Medical and Research Center, Denver, CO (US)

( * ) Notice: Subject to any disclaimer, the term of this patent is extended or adjusted under 35 U.S.C. 154(b) by 0 days.

(21) Appl. No.: 09/565,423

(22) Filed: May 5, 2000

Related U.S. Application Data

(60) Provisional application No. 60/132,892, filed on May 6, 1999, and provisional application No. 60/201,012, filed on May 1, 2000.

(51) Int. Cl.[7] .............................................. A61K 38/00
(52) U.S. Cl. ..................... 514/12; 530/350; 536/23.5; 435/69.1
(58) Field of Search ...................... 530/350; 536/23.5; 514/12; 435/69.1

(56) References Cited

U.S. PATENT DOCUMENTS

| | | | |
|---|---|---|---|
| 6,261,786 B1 | * | 7/2001 | Marigo et al. ................ 435/7.1 |
| 6,271,346 B1 | * | 8/2001 | Hauptmann et al. ......... 530/350 |

FOREIGN PATENT DOCUMENTS

| | | |
|---|---|---|
| EP | 0 869 180 A1 | 10/1998 |
| WO | WO98/18921 | 5/1998 |
| WO | WO 98/27114 | 7/1998 |
| WO | WO 99/12964 | 3/1999 |
| WO | WO 00/40716 | 7/2000 |
| WO | WO 0043032 | 7/2000 |
| WO | WO 00/47740 | 8/2000 |
| WO | WO 00/50597 | 8/2000 |
| WO | WO 01/12812 | 2/2001 |

OTHER PUBLICATIONS

Madry et al., Database SPTREMBL_16, Accession No. 088472, "Murine BCMA: a new member of the Tumor Necrosis Factor Receptor Superfamily". Nov. 1, 1998. (see attached sequence alignment).*
Gras et al., *Int'l Immunol.*, 7(7):1093–1106 (1995).
Gross et al., *Nature*, 404:995–999 (2000).
Khare et al., *Proc. Natl. Acad. Sci.USA*, 97(7):3370–5 (2000).
Laâbi et al., *EMBO J.*, 11(11):3897–3904 (1992).
Laâbi et al., *Nucleic Acids Res.*, 22(7):1147–1154 (1994).
Madry et al., *Int'l Immunol.*, 10(11):1693–1702 (1998).
Moore et al., *Science*, 285:260–263 (1999).
Mukhopadhyay et al., *J. Biol. Chem.*, 274(23):15987–15981 (1999).
Schneider et al., *J. Exp. Med.*, 189(11):1747–1756 (1999).
Shu et al., *J. Leukocyte Biology* 65:680–683 (1999).

* cited by examiner

*Primary Examiner*—Lorraine Spector
*Assistant Examiner*—Eileen B. O'Hara
(74) *Attorney, Agent, or Firm*—Sheridan Ross P.C.

(57) ABSTRACT

The amino acid and nucleic acid sequence of a protein expressed by monocytes and macrophages, called TALL-1, are disclosed. Homologues, mimetics and antibodies that bind to TALL-1 are disclosed. Also disclosed is the TALL-1 receptor, and homologues of such receptor. The invention includes methods for regulating the interaction between TALL-1 and its receptor and for identifying compounds capable of such regulation. The invention also includes methods for regulating B lymphocyte proliferation, activation, and/or survival.

19 Claims, 11 Drawing Sheets

| | | | |
|---|---|---|---|
| TALL-1 | 1 | MDDSTEREQSRLTSCLKKREEMKLKECVSI | 30 |
| TALL-2/APRIL | 1 | MPASSP--------------------FLL | 9 |

| | | | |
|---|---|---|---|
| TALL-1 | 31 | LPRKESPS-----VRSSKDGKLLAATLLA | 55 |
| TALL-2/APRIL | 10 | AP-KGPPGNMGGPVR----EPALSVALWLS | 34 |

| | | | |
|---|---|---|---|
| TALL-1 | 56 | LLSCLTVVSFYQVAALQGDLASLRAELQG | 85 |
| TALL-2/APRIL | 35 | WGAALGAVACAMALLTQQTELQSLRREVSR | 64 |

| | | | |
|---|---|---|---|
| TALL-1 | 86 | HHAEKLP--AGAGAPKAGLEEAPAVTAGLK | 113 |
| TALL-2/APRIL | 65 | LQGTGGPSQNGEGYPWQSLPEQ--SSDALE | 92 |

| | | | |
|---|---|---|---|
| TALL-1 | 114 | IFEPPAPGEGNSSQNSRNKRAVQGPEETVT | 143 |
| TALL-2/APRIL | 93 | AWE---NGER----SRKRRAVLTQKQKKQ | 114 |

| | | | |
|---|---|---|---|
| TALL-1 | 144 | QDCLQLIADSETPTIQKGS-YTFVPWLLSP | 172 |
| TALL-2/APRIL | 115 | HSVLHLVPINATSKDD--SDVTEVMWQPAL | 142 |

| | | | |
|---|---|---|---|
| TALL-1 | 173 | KRGSALEEKENKILVKETGYFFIYGQVLYT | 202 |
| TALL-2/APRIL | 143 | RRGRGLQAQGYGVRIQDAGVYLLYSQVLFQ | 172 |

| | | | |
|---|---|---|---|
| TALL-1 | 203 | DKTYAMGHLIQRKKVHVFGDELSLVTLFRC | 232 |
| TALL-2/APRIL | 173 | DVTFTMGQVVSRE------GQGRQETLFRC | 196 |

| | | | |
|---|---|---|---|
| TALL-1 | 233 | IQNMPETLP--NSCYSAGIAKLEEGDELQ | 260 |
| TALL-2/APRIL | 197 | IRSMPSHPDRAYNSCYSAGVFHLHQGDILS | 226 |

| | | | |
|---|---|---|---|
| TALL-1 | 261 | LAIPRENAQISLDGDVTFFGALKLL | 285 |
| TALL-2/APRIL | 227 | VIIPRARAKLNLSPHGTFLGFVKL | 250 |

FIG. 1A

```
TALL-1         144  QDCLQLIADSETPTIQ-----KGS----YT
TALL-2/APRIL   115  HSVLHLVPINATS--------KDDSDVTEV
TNF             87  KPVAHVVAN-----------PQAEGQ-----
FasL           144  RKVAHLTGK-----------SNSRSM-----
Lymphotoxin-α   62  KPAAHLIGD-----------PSKQNS-----
TRAIL          121  RVAAHITGTRGRSNTLSSPNSKNEKALGRK
                                  A TALL-1              FVPWLLSFKR---GSALEEKNKILVKETG
TALL-2/APRIL        MWQPALRRGRGLQAQGYGVR-----IQDAG
TNF                 -LQWLNRRANALLANGVELRDNQLVVPSEG
FasL                -PLEWEDTYGIVLLSGVKYKKGGLVINETG
Lymphotoxin-α       -LLWRANTDRAFLQDGFSLSNNSLLVPTSG
TRAIL               INSWESSRSGHSFLSNLHLRNGELVIHEKG
                       A'          A''    B'      B TALL-1              YFFIYGQVLYTDKTYAMGHLIQRKKVHVFG
TALL-2/APRIL        VYLLYSQVLFQDVTFTMGQVVSREGQGRQE
TNF                 LYLIYSQVLFKG----QGCPSTHVLLTHTI
FasL                LYFVYSKVYFRG------QSCNNLPLSHKV
Lymphotoxin-α       IYFVYSQVVFSGKAYSPKATSSPLYLAHEV
TRAIL               FYYIYSQTYFRFQEEIKENTKNDKQMVQYI
                           C                         D TALL-1              DELSLVTLFRCIQNMPETLPN---------
TALL-2/APRIL        TLFRCIRSMPSHPDRAYN------------
TNF                 SRIAVSYQTKVNLLSAIKSPCQRETPE-GA
FasL                YMRNSKYPQDLVMMEGKMMS-----YCT--
Lymphotoxin-α       QLFSSQYPFHVPLLSSQK----MVYPG---
TRAIL               YKYTSYPDPILLMKSARNS------CWSK
                                E TALL-1              ------NSCYSAGIAKLEEGD--ELQLAIP
TALL-2/APRIL        -------SCYSAGVFHLHQGD--ILSVIIP
TNF                 EAKPWYEPIYLGGVFQLEKGD--RLSAEIN
FasL                TGQMWARSSYLGAVFNLTSAD--HLYVNVS
Lymphotoxin-α       LQEPWLHSMYHGAAFQLTQGD--QLSTHTD
TRAIL               DAEYGLYSIYQGGIFELKENDRIFVSVTNE
                          F                      G TALL-1              RENAQISLDGDVTFFGALKLL  285
TALL-2/APRIL        RARAKLNLSPHGTFLGFVKL   250
TNF                 RPDYLDFAESGQVYFGIIAL   233
FasL                ELSLVNFEES-QTFFGLYKL   281
Lymphotoxin-α       GIPHLVLSPS-TVFFGAFAL   205
TRAIL               HLIDMDHEAS---FFGAFLVG  281
                                  H
```

FIG. 1B

SEQUENCE LISTING

<160> NUMBER OF SEQ ID NOS: 17

<210> SEQ ID NO 1
<211> LENGTH: 855
<212> TYPE: DNA
<213> ORGANISM: Artificial Sequence
<220> FEATURE:
<221> NAME/KEY: CDS
<222> LOCATION: (1)..(855)
<223> OTHER INFORMATION: Description of Artificial Sequence:primer

<400> SEQUENCE: 1

```
atg gat gac tcc aca gaa agg gag cag tca cgc ctt act tct tgc ctt        48
Met Asp Asp Ser Thr Glu Arg Glu Gln Ser Arg Leu Thr Ser Cys Leu
 1               5                  10                  15 aag aaa aga gaa gaa atg aaa ctg aag gag tgt gtt tcc atc ctc cca        96
Lys Lys Arg Glu Glu Met Lys Leu Lys Glu Cys Val Ser Ile Leu Pro
             20                  25                  30 cgg aag gaa agc ccc tct gtc cga tcc tcc aaa gac gga aag ctg ctg       144
Arg Lys Glu Ser Pro Ser Val Arg Ser Ser Lys Asp Gly Lys Leu Leu
         35                  40                  45 gct gca acc ttg ctg ctg gca ctg ctg tct tgc tgc ctc acg gtg gtg       192
Ala Ala Thr Leu Leu Leu Ala Leu Leu Ser Cys Cys Leu Thr Val Val
     50                  55                  60 tct ttc tac cag gtg gcc gcc ctg caa ggg gac ctg gcc agc ctc cgg       240
Ser Phe Tyr Gln Val Ala Ala Leu Gln Gly Asp Leu Ala Ser Leu Arg
 65                  70                  75                  80 gca gag ctg cag ggc cac cac gcg gag aag ctg cca gca gga gca gga       288
Ala Glu Leu Gln Gly His His Ala Glu Lys Leu Pro Ala Gly Ala Gly
                 85                  90                  95 gcc ccc aag gcc ggc ttg gag gaa gct cca gct gtc acc gcg gga ctg       336
Ala Pro Lys Ala Gly Leu Glu Glu Ala Pro Ala Val Thr Ala Gly Leu
            100                 105                 110 aaa atc ttt gaa cca cca gct cca gga gaa ggc aac tcc agt cag aac       384
Lys Ile Phe Glu Pro Pro Ala Pro Gly Glu Gly Asn Ser Ser Gln Asn
        115                 120                 125 agc aga aat aag cgt gcc gtt cag ggt cca gaa gaa aca gtc act caa       432
Ser Arg Asn Lys Arg Ala Val Gln Gly Pro Glu Glu Thr Val Thr Gln
    130                 135                 140 gac tgc ttg caa ctg att gca gac agt gaa aca cca act ata caa aaa       480
Asp Cys Leu Gln Leu Ile Ala Asp Ser Glu Thr Pro Thr Ile Gln Lys
145                 150                 155                 160 gga tct tac aca ttt gtt cca tgg ctt ctc agc ttt aaa agg gga agt       528
Gly Ser Tyr Thr Phe Val Pro Trp Leu Leu Ser Phe Lys Arg Gly Ser
                165                 170                 175 gcc cta gaa gaa aaa gag aat aaa ata ttg gtc aaa gaa act ggt tac       576
Ala Leu Glu Glu Lys Glu Asn Lys Ile Leu Val Lys Glu Thr Gly Tyr
            180                 185                 190 ttt ttt ata tat ggt cag gtt tta tat act gat aag acc tac gcc atg       624
```

```
Phe Phe Ile Tyr Gly Gln Val Leu Tyr Thr Asp Lys Thr Tyr Ala Met
            195                 200                 205
gga cat cta att cag agg aag aag gtc cat gtc ttt ggg gat gaa ttg      672
Gly His Leu Ile Gln Arg Lys Lys Val His Val Phe Gly Asp Glu Leu
        210                 215                 220
agt ctg gtg act ttg ttt cga tgt att caa aat atg cct gaa aca cta      720
Ser Leu Val Thr Leu Phe Arg Cys Ile Gln Asn Met Pro Glu Thr Leu
225                 230                 235                 240
ccc aat aat tcc tgc tat tca gct ggc att gca aaa ctg gaa gaa gga      768
Pro Asn Asn Ser Cys Tyr Ser Ala Gly Ile Ala Lys Leu Glu Glu Gly
                245                 250                 255
gat gaa ctc caa ctt gca ata cca aga gaa aat gca caa ata tca ctg      816
Asp Glu Leu Gln Leu Ala Ile Pro Arg Glu Asn Ala Gln Ile Ser Leu
        260                 265                 270
gat gga gat gtc aca ttt ttt ggt gca ttg aaa ctg ctg                  855
Asp Gly Asp Val Thr Phe Phe Gly Ala Leu Lys Leu Leu
            275                 280             285

<210> SEQ ID NO 2
<211> LENGTH: 285
<212> TYPE: PRT
<213> ORGANISM: Artificial Sequence
<220> FEATURE:
<223> OTHER INFORMATION: Description of Artificial Sequence:primer

<400> SEQUENCE: 2

Met Asp Asp Ser Thr Glu Arg Glu Gln Ser Arg Leu Thr Ser Cys Leu
 1               5                  10                  15
Lys Lys Arg Glu Glu Met Lys Leu Lys Glu Cys Val Ser Ile Leu Pro
            20                  25                  30
Arg Lys Glu Ser Pro Ser Val Arg Ser Lys Asp Gly Lys Leu Leu
        35                  40                  45
Ala Ala Thr Leu Leu Leu Ala Leu Leu Ser Cys Cys Leu Thr Val Val
    50                  55                  60
Ser Phe Tyr Gln Val Ala Ala Leu Gln Gly Asp Leu Ala Ser Leu Arg
65                  70                  75                  80
Ala Glu Leu Gln Gly His His Ala Glu Lys Leu Pro Ala Gly Ala Gly
                85                  90                  95
Ala Pro Lys Ala Gly Leu Glu Glu Ala Pro Ala Val Thr Ala Gly Leu
            100                 105                 110
Lys Ile Phe Glu Pro Pro Ala Pro Gly Glu Gly Asn Ser Ser Gln Asn
        115                 120                 125
Ser Arg Asn Lys Arg Ala Val Gln Gly Pro Glu Glu Thr Val Thr Gln
    130                 135                 140
Asp Cys Leu Gln Leu Ile Ala Asp Ser Glu Thr Pro Thr Ile Gln Lys
145                 150                 155                 160
Gly Ser Tyr Thr Phe Val Pro Trp Leu Leu Ser Phe Lys Arg Gly Ser
                165                 170                 175
Ala Leu Glu Glu Lys Glu Asn Lys Ile Leu Val Lys Glu Thr Gly Tyr
            180                 185                 190
Phe Phe Ile Tyr Gly Gln Val Leu Tyr Thr Asp Lys Thr Tyr Ala Met
        195                 200                 205
Gly His Leu Ile Gln Arg Lys Lys Val His Val Phe Gly Asp Glu Leu
    210                 215                 220
Ser Leu Val Thr Leu Phe Arg Cys Ile Gln Asn Met Pro Glu Thr Leu
225                 230                 235                 240
Pro Asn Asn Ser Cys Tyr Ser Ala Gly Ile Ala Lys Leu Glu Glu Gly
```

-continued

```
                245                 250                 255
Asp Glu Leu Gln Leu Ala Ile Pro Arg Glu Asn Ala Gln Ile Ser Leu
            260                 265                 270
Asp Gly Asp Val Thr Phe Phe Gly Ala Leu Lys Leu Leu
            275                 280             285

<210> SEQ ID NO 3
<211> LENGTH: 250
<212> TYPE: PRT
<213> ORGANISM: Homo sapiens

<400> SEQUENCE: 3

Met Pro Ala Ser Ser Pro Phe Leu Leu Ala Pro Lys Gly Pro Pro Gly
  1               5                  10                  15
Asn Met Gly Gly Pro Val Arg Glu Pro Ala Leu Ser Val Ala Leu Trp
             20                  25                  30
Leu Ser Trp Gly Ala Ala Leu Gly Ala Val Ala Cys Ala Met Ala Leu
         35                  40                  45
Leu Thr Gln Gln Thr Glu Leu Gln Ser Leu Arg Arg Glu Val Ser Arg
     50                  55                  60
Leu Gln Gly Thr Gly Gly Pro Ser Gln Asn Gly Glu Gly Tyr Pro Trp
 65                  70                  75                  80
Gln Ser Leu Pro Glu Gln Ser Ser Asp Ala Leu Glu Ala Trp Glu Asn
                 85                  90                  95
Gly Glu Arg Ser Arg Lys Arg Arg Ala Val Leu Thr Gln Lys Gln Lys
            100                 105                 110
Lys Gln His Ser Val Leu His Leu Val Pro Ile Asn Ala Thr Ser Lys
        115                 120                 125
Asp Asp Ser Asp Val Thr Glu Val Met Trp Gln Pro Ala Leu Arg Arg
    130                 135                 140
Gly Arg Gly Leu Gln Ala Gln Gly Tyr Gly Val Arg Ile Gln Asp Ala
145                 150                 155                 160
Gly Val Tyr Leu Leu Tyr Ser Gln Val Leu Phe Gln Asp Val Thr Phe
                165                 170                 175
Thr Met Gly Gln Val Val Ser Arg Glu Gly Gln Gly Arg Gln Glu Thr
            180                 185                 190
Leu Phe Arg Cys Ile Arg Ser Met Pro Ser His Pro Asp Arg Ala Tyr
        195                 200                 205
Asn Ser Cys Tyr Ser Ala Gly Val Phe His Leu His Gln Gly Asp Ile
    210                 215                 220
Leu Ser Val Ile Ile Pro Arg Ala Arg Ala Lys Leu Asn Leu Ser Pro
225                 230                 235                 240
His Gly Thr Phe Leu Gly Phe Val Lys Leu
                245                 250

<210> SEQ ID NO 4
<211> LENGTH: 147
<212> TYPE: PRT
<213> ORGANISM: Homo sapiens

<400> SEQUENCE: 4

Lys Pro Val Ala His Val Val Ala Asn Pro Gln Ala Glu Gly Gln Leu
  1               5                  10                  15
Gln Trp Leu Asn Arg Arg Ala Asn Ala Leu Leu Ala Asn Gly Val Glu
             20                  25                  30
Leu Arg Asp Asn Gln Leu Val Val Pro Ser Glu Gly Leu Tyr Leu Ile
```

```
              35                  40                  45
Tyr Ser Gln Val Leu Phe Lys Gly Gln Gly Cys Pro Ser Thr His Val
     50                  55                  60
Leu Leu Thr His Thr Ile Ser Arg Ile Ala Val Ser Tyr Gln Thr Lys
 65                  70                  75                  80
Val Asn Leu Leu Ser Ala Ile Lys Ser Pro Cys Gln Arg Glu Thr Pro
                 85                  90                  95
Glu Gly Ala Glu Ala Lys Pro Trp Tyr Glu Pro Ile Tyr Leu Gly Gly
            100                 105                 110
Val Phe Gln Leu Glu Lys Gly Asp Arg Leu Ser Ala Glu Ile Asn Arg
        115                 120                 125
Pro Asp Tyr Leu Asp Phe Ala Glu Ser Gly Gln Val Tyr Phe Gly Ile
    130                 135                 140
Ile Ala Leu
145

<210> SEQ ID NO 5
<211> LENGTH: 138
<212> TYPE: PRT
<213> ORGANISM: Homo sapiens

<400> SEQUENCE: 5

Arg Lys Val Ala His Leu Thr Gly Lys Ser Asn Ser Arg Ser Met Pro
 1               5                  10                  15
Leu Glu Trp Glu Asp Thr Tyr Gly Ile Val Leu Leu Ser Gly Val Lys
                20                  25                  30
Tyr Lys Lys Gly Gly Leu Val Ile Asn Glu Thr Gly Leu Tyr Phe Val
            35                  40                  45
Tyr Ser Lys Val Tyr Phe Arg Gly Gln Ser Cys Asn Asn Leu Pro Leu
     50                  55                  60
Ser His Lys Val Tyr Met Arg Asn Ser Lys Tyr Pro Gln Asp Leu Val
 65                  70                  75                  80
Met Met Glu Gly Lys Met Met Ser Tyr Cys Thr Thr Gly Gln Met Trp
                 85                  90                  95
Ala Arg Ser Ser Tyr Leu Gly Ala Val Phe Asn Leu Thr Ser Ala Asp
            100                 105                 110
His Leu Tyr Val Asn Val Ser Glu Leu Ser Leu Val Asn Phe Glu Glu
        115                 120                 125
Ser Gln Thr Phe Phe Gly Leu Tyr Lys Leu
    130                 135

<210> SEQ ID NO 6
<211> LENGTH: 144
<212> TYPE: PRT
<213> ORGANISM: Homo sapiens

<400> SEQUENCE: 6

Lys Pro Ala Ala His Leu Ile Gly Asp Pro Ser Lys Gln Asn Ser Leu
 1               5                  10                  15
Leu Trp Arg Ala Asn Thr Asp Arg Ala Phe Leu Gln Asp Gly Phe Ser
                20                  25                  30
Leu Ser Asn Asn Ser Leu Leu Val Pro Thr Ser Gly Ile Tyr Phe Val
            35                  40                  45
Tyr Ser Gln Val Val Phe Ser Gly Lys Ala Tyr Ser Pro Lys Ala Thr
     50                  55                  60
Ser Ser Pro Leu Tyr Leu Ala His Glu Val Gln Leu Phe Ser Ser Gln
```

```
                65                  70                  75                  80
Tyr Pro Phe His Val Pro Leu Leu Ser Ser Gln Lys Met Val Tyr Pro
                    85                  90                  95
Gly Leu Gln Glu Pro Trp Leu His Ser Met Tyr His Gly Ala Ala Phe
            100                 105                 110
Gln Leu Thr Gln Gly Asp Gln Leu Ser Thr His Thr Asp Gly Ile Pro
        115                 120                 125
His Leu Val Leu Ser Pro Ser Thr Val Phe Phe Gly Ala Phe Ala Leu
    130                 135                 140
```

<210> SEQ ID NO 7
<211> LENGTH: 161
<212> TYPE: PRT
<213> ORGANISM: Homo sapiens

<400> SEQUENCE: 7

```
Arg Val Ala Ala His Ile Thr Gly Thr Arg Gly Arg Ser Asn Thr Leu
 1               5                  10                  15
Ser Ser Pro Asn Ser Lys Asn Glu Lys Ala Leu Gly Arg Lys Ile Asn
                20                  25                  30
Ser Trp Glu Ser Ser Arg Ser Gly His Ser Phe Leu Ser Asn Leu His
            35                  40                  45
Leu Arg Asn Gly Glu Leu Val Ile His Glu Lys Gly Phe Tyr Tyr Ile
        50                  55                  60
Tyr Ser Gln Thr Tyr Phe Arg Phe Gln Glu Glu Ile Lys Glu Asn Thr
    65                  70                  75                  80
Lys Asn Asp Lys Gln Met Val Gln Tyr Ile Tyr Lys Tyr Thr Ser Tyr
                    85                  90                  95
Pro Asp Pro Ile Leu Leu Met Lys Ser Ala Arg Asn Ser Cys Trp Ser
            100                 105                 110
Lys Asp Ala Glu Tyr Gly Leu Tyr Ser Ile Tyr Gln Gly Gly Ile Phe
        115                 120                 125
Glu Leu Lys Glu Asn Asp Arg Ile Phe Val Ser Val Thr Asn Glu His
    130                 135                 140
Leu Ile Asp Met Asp His Glu Ala Ser Phe Phe Gly Ala Phe Leu Val
145                 150                 155                 160
Gly
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 8
ggaagcttat ggactacaag gacgacgatg                                    30

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 9
aaaggatcct acagacatgg tgtaagtag                                     29

-continued

```
<210> SEQ ID NO 10
<211> LENGTH: 834
<212> TYPE: DNA
<213> ORGANISM: Homo sapiens
<220> FEATURE:
<221> NAME/KEY: CDS
<222> LOCATION: (67)..(621)

<400> SEQUENCE: 10
ttgtaagata ttacttgtcc ttccaggctg ttctttctgt agctcccttg ttttcttttt        60 gtgatc atg ttg cag atg gct ggg cag tgc tcc caa aat gaa tat ttt         108
       Met Leu Gln Met Ala Gly Gln Cys Ser Gln Asn Glu Tyr Phe
       1               5                   10 gac agt ttg ttg cat gct tgc ata cct tgt caa ctt cga tgt tct tct         156
Asp Ser Leu Leu His Ala Cys Ile Pro Cys Gln Leu Arg Cys Ser Ser
15                  20                  25                  30 aat act cct cct cta aca tgt cag cgt tat tgt aat gca agt gtg acc         204
Asn Thr Pro Pro Leu Thr Cys Gln Arg Tyr Cys Asn Ala Ser Val Thr
                35                  40                  45 aat tca gtg aaa gga acg aat gcg att ctc tgg acc tgt ttg gga ctg         252
Asn Ser Val Lys Gly Thr Asn Ala Ile Leu Trp Thr Cys Leu Gly Leu
            50                  55                  60 agc tta ata att tct ttg gca gtt ttc gtg cta atg ttt ttg cta agg         300
Ser Leu Ile Ile Ser Leu Ala Val Phe Val Leu Met Phe Leu Leu Arg
        65                  70                  75 aag ata agc tct gaa cca tta aag gac gag ttt aaa aac aca gga tca         348
Lys Ile Ser Ser Glu Pro Leu Lys Asp Glu Phe Lys Asn Thr Gly Ser
    80                  85                  90 ggt ctc ctg ggc atg gct aac att gac ctg gaa aag agc agg act ggt         396
Gly Leu Leu Gly Met Ala Asn Ile Asp Leu Glu Lys Ser Arg Thr Gly
95                  100                 105                 110 gat gaa att att ctt ccg aga ggc ctc gag tac acg gtg gaa gaa tgc         444
Asp Glu Ile Ile Leu Pro Arg Gly Leu Glu Tyr Thr Val Glu Glu Cys
                115                 120                 125 acc tgt gaa gac tgc atc aag agc aaa ccg aag gtc gac tct gac cat         492
Thr Cys Glu Asp Cys Ile Lys Ser Lys Pro Lys Val Asp Ser Asp His
            130                 135                 140 tgc ttt cca ctc cca gct atg gag gaa ggc gca acc att ctt gtc acc         540
Cys Phe Pro Leu Pro Ala Met Glu Glu Gly Ala Thr Ile Leu Val Thr
        145                 150                 155 acg aaa acg aat gac tat tgc aag agc ctg cca gct gct ttg agt gct         588
Thr Lys Thr Asn Asp Tyr Cys Lys Ser Leu Pro Ala Ala Leu Ser Ala
    160                 165                 170 acg gag ata gag aaa tca att tct gct agg taa ttaaccattt cgactcgagc       641
Thr Glu Ile Glu Lys Ser Ile Ser Ala Arg
175                 180                 185 agtgccactt taaaatcttt tgtcagaat agatgatgtg tcagatctct ttaggatgac        701 tgtattttc agttgccgat acagcttttt gtcctctaac tgtggaaact ctttatgtta       761
gatatatttc tctaggttac tgttgggagc ttaatggtag aaacttcctt ggtttctatg       821
attaaagtct ttt                                                          834

<210> SEQ ID NO 11
<211> LENGTH: 184
<212> TYPE: PRT
<213> ORGANISM: Homo sapiens

<400> SEQUENCE: 11

Met Leu Gln Met Ala Gly Gln Cys Ser Gln Asn Glu Tyr Phe Asp Ser
1               5                   10                  15
```

```
Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Cys Thr Cys
            115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 12
ataagctttt tgtgatgatg ttg                                    23

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence:primer

<400> SEQUENCE: 13
ttggatcctt aagcgtaatc tggaacatcg tatgggtacc tagcagaaat tgat    54

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 14
gggaattcca tgttgcagat ggctg                                  25

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 15

-continued

```
ggggatccaa acaggtccag ag                                            22
```

<210> SEQ ID NO 16
<211> LENGTH: 558
<212> TYPE: DNA
<213> ORGANISM: Mus musculus
<220> FEATURE:
<221> NAME/KEY: CDS
<222> LOCATION: (1)..(558)

<400> SEQUENCE: 16

| | | | | | | | | | | | | | | | | |
|---|---|---|---|---|---|---|---|---|---|---|---|---|---|---|---|---|
| atg | gcg | caa | cag | tgt | ttc | cac | agt | gaa | tat | ttt | gac | agt | ctg | ctg | cat | 48 |
| Met | Ala | Gln | Gln | Cys | Phe | His | Ser | Glu | Tyr | Phe | Asp | Ser | Leu | Leu | His | |
| 1 | | | | 5 | | | | | 10 | | | | | 15 | | |
| gct | tgc | aaa | ccg | tgt | cac | ttg | cga | tgt | tcc | aac | cct | cct | gca | acc | tgt | 96 |
| Ala | Cys | Lys | Pro | Cys | His | Leu | Arg | Cys | Ser | Asn | Pro | Pro | Ala | Thr | Cys | |
| | | | 20 | | | | | 25 | | | | | 30 | | | |
| cag | cct | tac | tgt | gat | cca | agc | gtg | acc | agt | tca | gtg | aaa | ggg | acg | tac | 144 |
| Gln | Pro | Tyr | Cys | Asp | Pro | Ser | Val | Thr | Ser | Ser | Val | Lys | Gly | Thr | Tyr | |
| | | 35 | | | | | 40 | | | | | 45 | | | | |
| acg | gtg | ctc | tgg | atc | ttc | ttg | ggg | ctg | acc | ttg | gtc | ctc | tct | ttg | gca | 192 |
| Thr | Val | Leu | Trp | Ile | Phe | Leu | Gly | Leu | Thr | Leu | Val | Leu | Ser | Leu | Ala | |
| | 50 | | | | | 55 | | | | | 60 | | | | | |
| ctt | ttc | aca | atc | tca | ttc | ttg | ctg | agg | aag | atg | aac | ccc | gag | gcc | ctg | 240 |
| Leu | Phe | Thr | Ile | Ser | Phe | Leu | Leu | Arg | Lys | Met | Asn | Pro | Glu | Ala | Leu | |
| 65 | | | | | 70 | | | | | 75 | | | | | 80 | |
| aag | gac | gag | cct | caa | agc | cca | ggt | cag | ctt | gac | gga | tcg | gct | cag | ctg | 288 |
| Lys | Asp | Glu | Pro | Gln | Ser | Pro | Gly | Gln | Leu | Asp | Gly | Ser | Ala | Gln | Leu | |
| | | | | 85 | | | | | 90 | | | | | 95 | | |
| gac | aag | gcc | gac | acc | gag | ctg | act | agg | atc | agg | gct | ggt | gac | gac | agg | 336 |
| Asp | Lys | Ala | Asp | Thr | Glu | Leu | Thr | Arg | Ile | Arg | Ala | Gly | Asp | Asp | Arg | |
| | | | 100 | | | | | 105 | | | | | 110 | | | |
| atc | ttt | ccc | cga | agc | ctg | gag | tat | aca | gtg | gaa | gag | tgc | acc | tgt | gag | 384 |
| Ile | Phe | Pro | Arg | Ser | Leu | Glu | Tyr | Thr | Val | Glu | Glu | Cys | Thr | Cys | Glu | |
| | | 115 | | | | | 120 | | | | | 125 | | | | |
| gac | tgt | gtc | aag | agc | aaa | ccc | aag | ggg | gat | tct | gac | cat | ttc | ttc | ccg | 432 |
| Asp | Cys | Val | Lys | Ser | Lys | Pro | Lys | Gly | Asp | Ser | Asp | His | Phe | Phe | Pro | |
| | 130 | | | | | 135 | | | | | 140 | | | | | |
| ctt | cca | gcc | atg | gag | gag | ggg | gca | acc | att | ctt | gtc | acc | aca | aaa | acg | 480 |
| Leu | Pro | Ala | Met | Glu | Glu | Gly | Ala | Thr | Ile | Leu | Val | Thr | Thr | Lys | Thr | |
| 145 | | | | | 150 | | | | | 155 | | | | | 160 | |
| ggt | gac | tac | ggc | aag | tca | agt | gtg | cca | act | gct | ttg | caa | agt | gtc | atg | 528 |
| Gly | Asp | Tyr | Gly | Lys | Ser | Ser | Val | Pro | Thr | Ala | Leu | Gln | Ser | Val | Met | |
| | | | | 165 | | | | | 170 | | | | | 175 | | |
| ggg | atg | gag | aag | cca | act | cac | act | aga | taa | | | | | | | 558 |
| Gly | Met | Glu | Lys | Pro | Thr | His | Thr | Arg | | | | | | | | |
| | | | | 180 | | | | 185 | | | | | | | | |

<210> SEQ ID NO 17
<211> LENGTH: 185
<212> TYPE: PRT
<213> ORGANISM: Mus musculus

<400> SEQUENCE: 17

| Met | Ala | Gln | Gln | Cys | Phe | His | Ser | Glu | Tyr | Phe | Asp | Ser | Leu | Leu | His |
|---|---|---|---|---|---|---|---|---|---|---|---|---|---|---|---|
| 1 | | | | 5 | | | | | 10 | | | | | 15 | |

| Ala | Cys | Lys | Pro | Cys | His | Leu | Arg | Cys | Ser | Asn | Pro | Pro | Ala | Thr | Cys |
|---|---|---|---|---|---|---|---|---|---|---|---|---|---|---|---|
| | | | 20 | | | | | 25 | | | | | 30 | | |

| Gln | Pro | Tyr | Cys | Asp | Pro | Ser | Val | Thr | Ser | Ser | Val | Lys | Gly | Thr | Tyr |
|---|---|---|---|---|---|---|---|---|---|---|---|---|---|---|---|
| | | 35 | | | | | 40 | | | | | 45 | | | |

| Thr | Val | Leu | Trp | Ile | Phe | Leu | Gly | Leu | Thr | Leu | Val | Leu | Ser | Leu | Ala |
|---|---|---|---|---|---|---|---|---|---|---|---|---|---|---|---|

-continued

```
                50                          55                          60

Leu Phe Thr Ile Ser Phe Leu Leu Arg Lys Met Asn Pro Glu Ala Leu
 65                  70                  75                  80

Lys Asp Glu Pro Gln Ser Pro Gly Gln Leu Asp Gly Ser Ala Gln Leu
                 85                  90                  95

Asp Lys Ala Asp Thr Glu Leu Thr Arg Ile Arg Ala Gly Asp Asp Arg
                100                 105                 110

Ile Phe Pro Arg Ser Leu Glu Tyr Thr Val Glu Glu Cys Thr Cys Glu
            115                 120                 125

Asp Cys Val Lys Ser Lys Pro Lys Gly Asp Ser Asp His Phe Phe Pro
130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                165                 170                 175

Gly Met Glu Lys Pro Thr His Thr Arg
                180                 185
```

TALL-1 RECEPTOR HOMOLOGUES

CROSS-REFERENCE TO RELATED PATENT APPLICATIONS

This application claims priority under 35 U.S.C. §119(e) from U.S. Provisional Application Ser. No. 60/132,892, filed May 6, 1999, entitled, "TNF-Family TALL-1 Proteins, Nucleic Acid Molecules and Uses Thereof." This application also claims priority under 35 U.S.C. §119(e) from U.S. Provisional Application Ser. No. 60/201,012, filed May 1, 2000, entitled "TALL-1 Nucleic Acid Molecules, Proteins, Receptors and Methods of Use Thereof". The entire disclosures of U.S. Provisional Application Ser. No. 60/132,892 and U.S. Provisional Application Ser. No. 60/201,012 are incorporated herein by reference.

FIELD OF THE INVENTION

The present invention relates to ligand involved in B lymphocyte activation and proliferation, TALL-1, and to its receptor, TALL-1 receptor. More particularly, the present invention relates to TALL-1 and TALL-1 receptor, to homologues of such proteins, to nucleic acid molecules encoding such proteins, and to methods of making and using such proteins.

BACKGROUND OF THE INVENTION

Members of the tumor necrosis factor (TNF) ligand family play important roles in various physiological and pathological processes, including cell proliferation, differentiation, apoptosis, modulation of immune response and induction of inflammation (Smith et al., (1994), Cell 76:959–962; Grewal et al., (1996), The role of CD40 ligand in immunity and auto-immunity. Page 125–134. In Immune Tolerance, editors: J. Banchereau, B. Dodet, R. Schwartz, E. Trannoy. Elsevier Press: Paris.; Nataga, (1997), Cell 88:355–365; Baker et al., (1998), Onocogene 17:3261–3270; Ashkenazi et al., (1999), Curr. Opin. Cell Biol. 11:255–260). At least sixteen members of the TNF ligand family have been identified. These include TNF, FasL, Lymphotoxin-α, Lymphotoxin-β, TRA1L/APO-2L, CD27L, CD30L, CD40L, 4-1BBL, OX40L, TRANCE/ RANKL, LIGHT, TWEAK, TL 1, APRIL/TALL-2 and TALL-1 (Smith et al., (1994), Cell 76:959–962; Grewal et al., (1996), The role of CD40 ligand in immunity and auto-immunity. Page 125–134. In Immune Tolerance, editors: J. Banchereau, B. Dodet, R. Schwartz, E. Trannoy. Elsevier Press: Paris.; Nataga, (1997), Cell 88:355–365; Baker et al., (1998), Onocogene 17:3261–3270; Ashkenazi et al., (1999), Curr. Opin. Cell Biol. 11:255–260; Shu et al., (1999), J. Leukocyte Biology 65:680–683; Schneider et al., (1999), J. Exp. Med. 189:1747–1756; Moore et al., (1999), Science 285:260–263; Mukhopadhyay et al., (1 999), J. Biol. Chem. 274:15978–15981). Most TNF family members are synthesized as type II transmembrane precursors. Their extracellular domains can be cleaved by metalloproteinases to form soluble cytokines. The soluble and membrane-bound TNF ligand family members bind to receptors belonging to the TNF receptor family, which are type I transmembrane proteins with characteristic cysteine rich motifs (Smith et al., (1994), Cell 76:959–962; Nataga, (1997), Cell 88:355–365; Baker et al., (1998), Onocogene 17:3261–3270; Ashkenazi et al., (1999), Curr. Opin. Cell Biol. 11:255–260).

Members of the TNF family interact with their cognate receptors either through cell-cell interactions or as soluble proteins after their extracellular domains are cleaved by metalloproteinases (Smith et al., (1 994),Cell 76:959–962; Nataga, (1 997), Cell 88:355 –365). The TNF receptor family contains about 20 members. Stimulation of TNF receptor family members by their ligands triggers overlapping and divergent intracellular signal transduction pathways, including those that lead to apoptosis, NF-κB and AP1 activation (Smith et al., (1994), Cell 76:959–962; Nataga, (1997), Cell 88:355–365). Therefore regulation of TNF family members that specifically affect immune responses is desirable.

A wide variety of medical treatments require regulation of the immune response in a patient. Such treatments include, for example, vaccinations, treatments for autoimmune diseases, immunodeficiency diseases, immunoproliferative diseases, and treatments involving the transplantation of organs and skin. Traditional reagents and methods used to regulate a subject's immune response often results in unwanted side effects. For example, immunosuppressive reagents such as cyclosporin A, azathioprine, and prednisone are used to suppress the immune system of a patient with an autoimmune disease or patients receiving transplants. Such reagents, however, suppress a patient's entire immune response, thereby crippling the ability of the patient to mount an immune response against infectious agents not involved in the original disease. Due to such harmful side effects and the medical importance of immune regulation, reagents and methods to regulate specific parts of the immune system have been the subject of study for many years.

The present invention can be used to overcome traditional problems with immunoregulatory reagents by more specifically regulating cells, ligands and receptors of the immune system in vivo.

SUMMARY OF THE INVENTION

The present invention generally relates to TALL-1 nucleic acid molecules, proteins (including homologues), antibodies, and methods of making and using the same. The present invention also relates to TALL-1 receptor nucleic acid molecules, proteins (including homologues), antibodies, and methods of using the same. In particular, the present invention relates to methods of regulating the interaction between TALL-1 and the TALL-1 receptor to regulate monocyte, macrophage and B lymphocyte mediated immune responses.

One embodiment of the present invention relates to an isolated TALL-1 protein. Preferably, the isolated TALL-1 protein comprises an amino acid sequence selected from the group of: (a) SEQ ID NO:2; and (b) a homologue of SEQ ID NO:2. The homologue comprises an amino acid sequence selected from the group of: (i) an amino acid sequence that is at least about 40% identical to SEQ ID NO:2 over at least 175 amino acids of SEQ ID NO:2; and, (ii) an amino acid sequence that is at least about 40% identical to SEQ ID NO:2 over positions 134–285 of SEQ ID NO:2. In a more preferred embodiment, the protein comprises an amino acid sequence selected from the group of: (a) an amino acid sequence that is at least about 60% identical to SEQ ID NO:2 over at least 175 amino acids of SEQ ID NO:2; and, (b) an amino acid sequence that is at least about 60% identical to SEQ ID NO:2 over positions 134–285 of SEQ ID NO:2. In an even more preferred embodiment, the protein comprises an amino acid sequence selected from the group of: (a) an amino acid sequence that is at least about 80% identical to SEQ ID NO:2 over at least 175 amino acids of SEQ ID NO:2; and, (b) an amino acid sequence that is at least about 80% identical to SEQ ID NO:2 over positions 134–285 of SEQ ID NO:2. In an even more preferred embodiment, the protein comprises an amino acid sequence selected from the group consisting of: (a) an amino acid sequence that is at least about 90% identical to SEQ ID NO:2 over at least 175 amino acids of SEQ ID NO:2; and, (b) an amino acid sequence that is at least about 90% identical to SEQ ID NO:2 over positions 134–285 of SEQ ID NO:2.

In another embodiment, the isolated TALL-1 protein of the present invention has an amino acid sequence comprising at least about 30 contiguous amino acids of SEQ ID NO:2. Preferably, the protein has an amino acid sequence comprising at least about 50 contiguous amino acids of SEQ ID NO:2, and more preferably, at least about 130 contiguous amino acids of SEQ ID NO:2. In a particularly preferred embodiment, the protein comprises amino acid residues 134 through 285 of SEQ ID NO:2. In another particularly preferred embodiment, the protein comprises an amino acid sequence represented by SEQ ID NO:2.

In another embodiment, the isolated TALL-1 protein of the present invention is encoded by a nucleic acid molecule comprising a nucleic acid sequence that hybridizes under low stringency conditions, and preferably, moderate stringency conditions, and more preferably, high stringency conditions, to the complement of a nucleic acid sequence represented by SEQ ID NO:1. In a particularly preferred embodiment, the protein is encoded by a nucleic acid molecule comprising a nucleic acid sequence represented by SEQ ID NO:1. In another particularly preferred embodiment, the protein is encoded by a nucleic acid molecule comprising a nucleic acid sequence represented by nucleotide positions 402 through 855 of SEQ ID NO:1.

In one embodiment of the present invention, an isolated TALL-1 protein is soluble. In another embodiment, the isolated TALL-1 protein is a membrane protein. Preferably, the isolated TALL-1 protein of the present invention has TALL-1 biological activity. Such biological activities include, but are not limited to: (a) binding to a TALL-1 receptor; (b) costimulation of B lymphocyte proliferation; (c) costimulation of B lymphocyte activation; and/or (d) support of B lymphocyte survival. Preferably, the isolated TALL-1 protein binds to a TALL-1 receptor. In one embodiment, a TALL-1 protein binds to an activates a TALL-1 receptor. In another embodiment, the TALL-1 protein is a TALL-1 homologue that does not activate a TALL-1 receptor.

Yet another embodiment of the present invention relates to an isolated antibody that specifically binds to the isolated TALL-1 protein of the present invention.

Another embodiment of the present invention relates to an isolated nucleic acid molecule comprising a nucleic acid sequence encoding a protein comprising an amino acid sequence selected from the group of: (a) SEQ ID NO:2; and, a homologue of SEQ ID NO:2. The homologue comprises an amino acid sequence selected from the group consisting of: (i) an amino acid sequence comprising at least 130 contiguous amino acids of SEQ ID NO:2; and, (ii) an amino acid sequence comprising at least positions 134–285 of SEQ ID NO:2. Preferably, the homologue comprises an amino acid sequence comprising at least 150 contiguous amino acids of SEQ ID NO:2, and even more preferably, the homologue comprises an amino acid sequence comprising at least 175 contiguous amino acids of SEQ ID NO:2. In a particularly preferred embodiment, the nucleic acid sequence encodes a protein comprising an amino acid sequence represented by SEQ ID NO:2, or a protein comprising an amino acid sequence comprising amino acids 134–285 of SEQ ID NO:2.

Preferably, the isolated nucleic acid sequence comprises at least 390 contiguous nucleotides of SEQ ID NO:1. In another aspect, the nucleic acid sequence hybridizes under low stringency conditions, and preferably, moderate stringency conditions, and more preferably, high stringency conditions, to the complement of a nucleic acid sequence SEQ ID NO:1. In a particularly preferred embodiment, the nucleic acid sequence comprises SEQ ID NO:1, or the nucleic acid sequence comprises nucleotides 402 through 855 of SEQ ID NO:1.

One embodiment of the present invention relates to an isolated nucleic acid molecule as set forth above, operatively linked to a transcription control sequence. Another embodiment of the present invention relates to a recombinant cell comprising an isolated nucleic acid molecule as set forth above, wherein the cell expresses the recombinant nucleic acid molecule. Yet another embodiment of the present invention relates to a recombinant virus, comprising an isolated nucleic acid molecule as set forth above.

Yet another embodiment of the present invention relates to a recombinant nucleic acid molecule comprising an expression vector operatively linked to a nucleic acid molecule comprising a nucleic acid sequence encoding a protein having TALL-1 biological activity. The protein comprises an amino acid sequence selected from the group of: (a) SEQ ID NO:2; and, (b) a homologue of SEQ ID NO:2, wherein the homologue comprises an amino acid sequence selected from the group of: (i) an amino acid sequence that is at least about 40% identical to SEQ ID NO:2 over at least 175 amino acids of SEQ ID NO:2; and, (ii) an amino acid sequence that is at least about 40% identical to SEQ ID NO:2 over positions 134–285 of SEQ ID NO:2.

Another embodiment of the present invention relates to a method to produce a TALL-1 protein. Such a method includes the step of culturing an isolated cell to express any of the recombinant nucleic acid molecules described above, under conditions whereby a TALL-1 protein encoded by the recombinant nucleic acid molecule is produced.

Yet another embodiment of the present invention relates to an isolated TALL-1 receptor homologue, wherein the homologue comprises an amino acid sequence that is: (a) at least about 40% identical to SEQ ID NO:11 over at least 35 amino acids of SEQ ID NO:11; and, (b) less than 100% identical to an amino acid sequence selected from the group of SEQ ID NO:11 and SEQ ID NO:17. In a preferred embodiment, the TALL-1 receptor homologue is at least about 65% identical to SEQ ID NO:1, and more preferably, the homologue is at least about 75% identical to SEQ ID NO:11, and more preferably, the homologue is at least about 90% identical to SEQ ID NO:11. In one embodiment of the present invention, the homologue is less than about 95% identical to the amino acid sequence selected from the group of SEQ ID NO:11 and SEQ ID NO:17; in another embodiment, the homologue is less than about 90% identical to the amino acid sequence selected from the group consisting of SEQ ID NO:11 and SEQ ID NO:17.

In one embodiment, the TALL-1 receptor homologue encoded by a nucleic acid molecule comprising a nucleic acid sequence that hybridizes under moderate stringency conditions to the complement of SEQ ID NO:10, and more preferably, the homologue is encoded by a nucleic acid molecule comprising a nucleic acid sequence that hybridizes under high stringency conditions to the complement of SEQ ID NO:10.

In one embodiment, the TALL-1 receptor homologue binds to TALL-1. In one embodiment, the homologue is a soluble TALL-1 receptor. In another embodiment, the homologue does not bind to TALL-1. In another embodiment, the homologue activates NF-κB in a cell expressing the homologue through a TRAF5, TRAF6, NIK, IKKα and IKKβ dependent pathway. In one embodiment, the homologue costimulates B lymphocyte proliferation in a B lymphocyte expressing the homologue.

Yet another embodiment of the present invention relates to an isolated nucleic acid molecule comprising a nucleic acid sequence encoding a TALL-1 receptor homologue. The homologue comprises an amino acid sequence that is: (a) at least about 40% identical to SEQ ID NO:11 over at least 35 amino acids of SEQ ID NO:11; and, (b) less than 100% identical to an amino acid sequence selected from the group of SEQ ID NO:11 and SEQ ID NO:17.

Another embodiment of the present invention relates to a composition comprising: (a) a compound; and (b) a pharmaceutically acceptable carrier. The compound of (a) is selected from the group of: (i) an isolated TALL-1 protein; (ii) an isolated antibody that selectively binds to the TALL-1 protein of (i); (iii) an isolated TALL-1 receptor; and, (iv) an isolated antibody that selectively binds to the TALL-1 receptor of (iii).

In one aspect of the composition of the present invention, the compound is an isolated TALL-1 protein. Such a TALL-1 protein can be any heretofore described TALL-1 protein, including a protein comprising an amino acid sequence selected from the group of: (a) SEQ ID NO:2; and, (b) a homologue of SEQ ID NO:2, wherein the homologue comprises an amino acid sequence selected from the group of: (i) an amino acid sequence that is at least about 40% identical to SEQ ID NO:2 over at least 175 amino acids of SEQ ID NO:2; and, (ii) an amino acid sequence that is at least about 40% identical to SEQ ID NO:20 over positions 134–285 of SEQ ID NO:2. In one embodiment, the isolated TALL-1 protein is encoded by a nucleic acid sequence that hybridizes under moderate stringency conditions to the complement of a nucleic acid sequence encoding SEQ ID NO:2. In another embodiment, the isolated TALL-1 protein comprises an amino acid sequence represented by SEQ ID NO:2.

In another aspect of he composition of the present invention, the compound is an isolated TALL-1 receptor. In one embodiment, the receptor is a soluble TALL-1 receptor. In another embodiment, the receptor comprises an amino acid sequence selected from the group of: (a) SEQ ID NO:1; and, (b) a TALL-1 receptor homologue comprising an amino acid sequence that is: (i) at least about 40% identical to SEQ ID NO:11 over at least 35 amino acids of SEQ ID NO:11; and, (ii) less than 100% identical to an amino acid sequence selected from the group of SEQ ID NO:11 and SEQ ID NO:17.

Yet another embodiment of the present invention relates to a method to activate a TALL-1 receptor, comprising contacting a TALL-1 receptor with a TALL-1 protein. Preferably, the TALL-1 protein comprises an amino acid sequence selected from the group of: (a) SEQ ID NO:2; and, (b) a homologue of SEQ ID NO:2, wherein the homologue comprises an amino acid sequence selected from the group of: (i) an amino acid sequence that is at least about 40% identical to SEQ ID NO:2 over at least 175 amino acids of SEQ ID NO:2; and, (ii) an amino acid sequence that is at least about 40% identical to SEQ ID NO:2 over positions 134–285 of SEQ ID NO:2.

Another embodiment of the present invention relates to a method to regulate B lymphocyte proliferation, activation, and/or survival, comprising regulating the biological activity of a TALL-1 receptor expressed by a B lymphocyte. In one aspect, the step of regulating comprises inhibiting the biological activity of the TALL-1 receptor. For example, the step of regulating can include inhibiting the interaction of TALL-1 with the TALL-1 receptor. In one aspect of this embodiment, the step of inhibiting comprises contacting TALL-1 expressed by a monocyte or macrophage with a compound that inhibits binding of the TALL-1 to the TALL-1 receptor. Such a compound can include, but is not limited to: (a) an antibody that selectively binds to TALL-1 and inhibits the binding of TALL-1 to the TALL-1 receptor; (b) a soluble TALL-1 receptor; and, (c) a TALL-1 receptor homologue, wherein the homologue comprises an amino acid sequence that is at least about 40% identical over at least 35 amino acids to SEQ ID NO:11, wherein the homologue binds to TALL-1, and wherein the receptor does not activate NF-κB when expressed by a cell. In one aspect, the compound is preferably a soluble TALL-1 receptor.

In another aspect of this embodiment, the step of inhibiting comprises contacting the TALL-1 receptor with a compound that inhibits the interaction of TALL-1 with the TALL-1 receptor. Such a compound can include, but is not limited to: (a) an antibody that selectively binds to the TALL-1 receptor and inhibits the binding of the TALL-1 receptor by TALL-1 ; and/or (b) a TALL-1 homologue, wherein the homologue comprises an amino acid sequence selected from the group of: (i) an amino acid sequence that is at least about 40% identical to SEQ ID NO:2 over at least 175 amino acids of SEQ ID NO:2; and, (ii) an amino acid sequence that is at least about40% identical to SEQ ID NO:2 over positions 134–285 of SEQ ID NO:2. In this aspect, the homologue binds to the TALL-1 receptor but does not activate the TALL-1 receptor.

In another aspect of the method of the present invention, the step of regulating comprises stimulating the biological activity of the TALL-1 receptor. In one aspect, the method includes the step of contacting the TALL-1 receptor with a compound that increases TALL-1 receptor activity. Such a compound can include, but is not limited to: (a) an isolated TALL-1 protein; and, (b) an antibody that selectively binds to the TALL-1 receptor and activates the receptor. Preferably, the isolated TALL-1 protein comprises an amino acid sequence selected from the group of: (a) SEQ ID NO:2; and, (b) a homologue of SEQ ID NO:2, wherein the homologue comprises an amino acid sequence selected from the group of: (i) an amino acid sequence that is at least about 40% identical to SEQ ID NO:2 over at least 175 amino acids of SEQ ID NO:2; and, (ii) an amino acid sequence that is at least about 40% identical to SEQ ID NO:2 over positions 134–285 of SEQ ID NO:2.

In one aspect of the method of the present invention, the regulation of B lymphocyte proliferation, activation and/or survival by the method is effective to regulate a B-lymphocyte immune response in an animal. In another aspect of the method of the present invention, the inhibition of B lymphocyte proliferation, activation and/or survival by the method is effective to inhibit a B lymphocyte-associated autoimmune disease.

Yet another embodiment of the present invention relates to a method to inhibit a B lymphocyte immune response in a patient, comprising inhibiting the interaction of TALL-1 with a TALL-1 receptor in the patient. Another embodiment of the present invention relates to a method to inhibit a B lymphocyte-associated autoimmune disease in a patient, comprising inhibiting the interaction of TALL-1 with a TALL-1 receptor in the patient.

Yet another embodiment of the present invention relates to a method to identify compounds that regulate the interaction between TALL-1 and a TALL-1 receptor. Such a method includes the steps of: (a) contacting a TALL-1 receptor with a putative regulatory compound; (b) contacting the TALL-1 receptor with a TALL-1 protein comprising an amino acid sequence selected from the group of: (i) SEQ ID NO:2; and, (ii) a homologue of SEQ ID NO:2, wherein the homologue comprises an amino acid sequence selected from the group of: (1) an amino acid sequence that is at least about 40% identical to SEQ ID NO:2 over at least 175 amino acids of SEQ ID NO:2; and, (2) an amino acid sequence that is at least about 40% identical to SEQ ID NO:2 over positions 134–285 of SEQ ID NO:2 or a homologue of TALL-1; and (c) detecting whether the putative regulatory compound regulates the TALL-1 receptor. The TALL-1 protein binds to and activates the TALL-1 receptor in the absence of the putative regulatory compound. In one aspect, the step of detecting comprises detecting whether the putative regulatory compound inhibits the binding of the TALL-1 protein to the TALL-1 receptor. In another aspect, the step of detecting comprises detecting whether the putative regulatory compound inhibits the activation of the TALL-1 receptor as compared to in the absence of the putative regulatory compound.

BRIEF DESCRIPTION OF THE FIGURES OF THE INVENTION

FIG. 1A is an amino acid sequence alignment of human TALL-1 and human TALL-2/APRIL.

FIG. 1B is an amino acid sequence alignment of full-length human TALL-1 and TALL-2/APRIL with other TNF family members.

DETAILED DESCRIPTION OF THE INVENTION

Figure 2A:
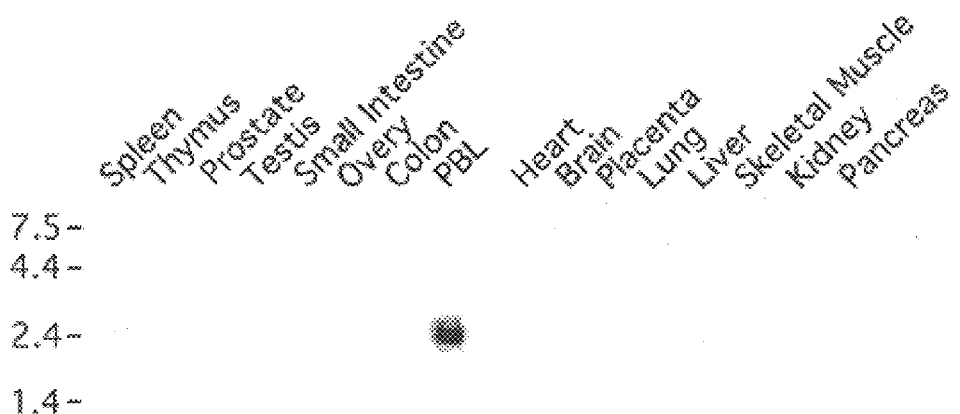
FIG. 2A is a digitized image of a Northern blot analysis showing Tall-1 gene expression in human tissues.

The present invention generally relates to isolated nucleic acid sequences encoding TALL-1, to isolated nucleic acid molecules comprising nucleic acid sequences encoding TALL-1 (including recombinant nucleic acid molecules), to homologues of such nucleic acid sequences, to TALL-1 proteins and fusion proteins and homologues thereof, to polyclonal and monoclonal antibodies that specifically bind to TALL-1 and/or homologues or mimetics thereof, and to methods of using such nucleic acid molecules, proteins and antibodies. The present invention also includes receptors that are bound by TALL-1, referred to herein as TALL-1 receptors. Also included in the present invention are homologues and mimetics of TALL-1 that bind to and regulate (upregulate or downregulate) the activity of a TALL-1 receptor, as well as TALL-1 receptor homologues.

The present invention also includes methods which use nucleic acid sequences encoding TALL-1, TALL-1 proteins (including TALL-1 homologues), TALL-1 antibodies, and TALL-1 receptors (including TALL-1 receptor homologues) and TALL-1 receptor antibodies as therapeutic reagents and/or diagnostic tools. As such, one embodiment of the present invention relates to a method to identify regulators of TALL-1 by identifying putative regulatory compounds which increase or decrease the action (i.e., expression and/or biological activity) of TALL-1 proteins or nucleic acid molecules and/or TALL-1 receptor proteins or nucleic acid molecules. Another embodiment of the present invention relates to a method to regulate biological processes, including immune processes, that are mediated by monocytes, macrophages, and/or B lymphocytes. Another embodiment of the present invention relates to a method to identify regulators of biological processes, including immune processes, that are mediated by monocytes, macrophages, and/or B lymphocytes. Yet another embodiment of the present invention relates to therapeutic compositions comprising one or more of TALL-1 proteins, nucleic acid molecules comprising nucleic acid sequence encoding TALL-1, antibodies that specifically bind to TALL-1, inhibitors of TALL-1 proteins, TALL-1 receptor proteins, nucleic acid molecules comprising nucleic acid sequence encoding TALL-1 receptor, antibodies that specifically bind to TALL-1 receptor, and/or inhibitors of TALL-1 receptor, that are useful in a method of regulating biological processes, including immune processes, that are mediated by monocytes, macrophages, and/or B lymphocytes. Yet another embodiment relates to a method to diagnose disorders related to the biological activity and/or expression (or disregulation thereof) of TALL-1.

TALL-1 is a novel TNF family member identified by the present inventors (Shu et al., (1999), *J. Leukocyte Biology* 65:680–683) and subsequently published by three other groups (Schneider et al., (1999), *J. Exp. Med.* 189:1747–1756; Moore et al., (1999), *Science* 285:260–263; Mukhopadhyay et al., (1999), *J. Biol. Chem.* 274:15978–15981). Unlike most members of the TNF family which are expressed by activated immune cells, TALL-1 is constitutively expressed by monocytes and macrophages (Shu et al., (1999), *J. Leukocyte Biology* 65:680–683; Schneider et al., (1999), *J. Exp. Med.* 189:1747–1756). Flow cytometry analysis indicates that the receptor for TALL-1 is expressed only by peripheral B lymphocytes or B lymphocyte-derived cell lines, but not by peripheral T lymphocytes, monocytes, and non-B lymphocyte-derived cell lines (Schneider et al., (1999), *J. Exp. Med.* 189:1747–1756; Moore et al., (1999), *Science* 285:260–263). Functional studies indicate that soluble TALL-1 (sTALL-1) co-stimulates B lymphocyte proliferation in vitro and administration or overexpression of sTALL-1 causes lymphocytic disorders and autoimmune manifestations in mice (Moore et al., (1999), *Science* 285:260–263; Macky et al., (1999), *J. Exp. Med.* 190:1697–1710). These data suggest that TALL-1 plays an important role in monocyte/macrophage-driven B lymphocyte activities.

The present inventors have also identified the receptor for TALL-1 (e.g., the TALL-1 receptor). The present inventors have discovered that B cell maturation factor, or BCMA, a previously described member of the TNF receptor family of unknown function which is specifically expressed by B lymphocytes, is the receptor for TALL-1. The present inventors have additionally discovered that BCMA can activate the transcription factor NF-κB through a TRAF5, TRAF6, NIK, IKKα and IKKβ dependent pathway. The identification of BCMA as the TALL-1 receptor is quite unexpected because, prior to the present invention, investigators studying BCMA reported that the factor was enriched in the Golgi apparatus, but failed to detect BCMA on the plasma membrane (Gras et al., (1995), *International Immunology* 7:1093–1106). In addition, prior sequence analysis suggested that BCMA had no recognizable signal peptide at its N-terminus (Laabi et al., (1992), *EMBO J.* 11:3897–3904; Laabi et al., (1994), *Nucleic Acids Research* 22:1147–1154; Gras et al., (1995), *International Immunology* 7:1093–1106) and therefore, it would not be expected to be inserted into the plasma membrane. The discovery of TALL-1 and of the ligand-receptor relationship between TALL-1 and BCMA (i.e., TALL-1 receptor) as well as the biological activities resulting from such a relationship, leads to methods of using both TALL-1 and BCMA, as well as homologues thereof, which were not previously possible or realized.

Various embodiments of the present invention are described below initially with regard to an isolated TALL-1 protein of the present invention. It is to be understood, however, that the general definitions of terms and methods are intended to apply to the discussion of an isolated TALL-1 receptor, also discussed below, unless otherwise modified within the specific discussion of the TALL-1 receptor.

Accordingly, one embodiment of the present invention relates to an isolated TALL-1 protein. As used herein, reference to an isolated protein, including an isolated TALL-1 protein, includes full-length proteins, fusion proteins, or any homologue of such a protein. In one embodiment, an isolated TALL-1 protein is a membrane protein. In another embodiment, an isolated TALL-1 protein is a soluble protein (sTALL-1). An amino acid sequence for soluble TALL-1 spans from amino acid positions 134 to 285 of SEQ ID NO:2. It is noted that investigators who published proteins having the same amino acid sequence as TALL-1 subsequent to the filing of the priority application for the present invention have given the TALL-1 proteins different names, including: B lymphocyte stimulator (Blys)(Moore et al., July 1999, *Science* 285:260–263), tumor necrosis factor-like protein ZTNF4 (Submitted to GenBank on Sep. 14, 1999, by Biomolecular Informatics, Zymogenetics; released on Jan. 13, 2000), THANK (Mukhopadhyay et al., 1999, *J. Biol. Chem.* 274:15978–15981), and B-cell activating factor (BAFF) (Schneider et al., June 1999, *J. Exp. Med.* 189:1747–1756). According to the present invention, a homologue of a TALL-1 protein (i.e., a TALL-1 homologue) includes TALL-1 proteins in which at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). Preferably, a TALL-1 homologue has TALL-1 biological activity. TALL-1 biological activity is defined herein as at least one of: an ability to bind to a TALL-1 receptor; an ability to costimulate B lymphocyte proliferation; an ability to costimulate B lymphocyte activation; and/or an ability to support B lymphocyte survival. In one embodiment, a TALL-1 homologue comprises a portion of a wild-type TALL-1 protein sufficient to form β strands. Such portions are illustrated, for example, in FIG. 1B. In another embodiment, a TALL-1 homologue comprises at least the amino acid residues (in the equivalent positions) which are identical in the C-terminal region of several TNF family proteins as illustrated in FIG. 1B. Such a homologue also preferably binds specifically to a TALL-1 receptor, preferably such that the TALL-1 receptor is activated. It is noted that reference to a TALL-1 protein is intended to encompass variants of the TALL-1 sequence, including truncated TALL-1 proteins, in which conservative amino acid deletions, additions or substitutions are allowed which do not substantially change the biological activity of the TALL-1 protein with regard to at least one or more of the biological activities of TALL-1 as described above. Using the guidance provided herein, it is within the ability of one of skill in the art to make modifications in the nucleic acid and/or amino acid sequence of wild-type TALL-1 (e.g., SEQ ID NOs:1 or 2) and to test homologues having such modifications for one or more biological activities of TALL-1. For example, methods for determining binding of TALL-1 to TALL-1 receptor are described in detail in the Examples section and below with regard to the description of assays for evaluating regulators of the interaction between TALL-1 and TALL-1 receptor. In addition, biological and molecular assays for determining the activation of a TALL-1 receptor as a result of ligation, including B cell proliferation assays, NFκB activation and activation of other intracellular molecules is described in the Examples section. More specifically, methods of detecting and measuring TALL-1 biological activity include, but are not limited to measurement of transcription of TALL-1, measurement of translation of TALL-1, measurement of secretion of soluble TALL-1 (sTALL-1), measurement of binding of TALL-1 to a TALL-1 receptor, measurement of an increase in B cell proliferation, measurement of an increase in B cell activation, measurement of B cell survival. In another embodiment, a TALL-1 homologue may or may not have measurable TALL-1 activity, but is used for the preparation of antibodies or the development of oligonucleotides useful for identifying other TALL-1 proteins, or for use in diagnostic assays (described below). In one embodiment of the present invention, a TALL-1 homologue that is useful in a method of the present invention binds to, but does not activate, a TALL-1 receptor, and therefore serves as a competitive inhibitor of a wild-type TALL-1 protein.

In one embodiment, a TALL-1 protein (e.g., a TALL-1 protein homologue) comprises an amino acid sequence that is at least about 40% identical to SEQ ID NO:2 over at least about 175 contiguous amino acids of SEQ ID NO:2. In another embodiment, a TALL-1 protein comprises an amino acid sequence that is at least about 40% identical to SEQ ID NO:2 over positions 134–285 of SEQ ID NO:2. Preferably, a TALL-1 protein comprises an amino acid sequence that is at least about 50%, and more preferably, at least about 60%, and more preferably, at least about 70%, and more preferably at least about 80%, and more preferably at least about 90%, and even more preferably at least about 95% identical to SEQ ID NO:2 over at least about 175 amino acids of SEQ ID NO:2, and more preferably over at least about 200 amino acids, and more preferably over at least about 225 amino acids, and more preferably over at least about 250 amino acids, and even more preferably over 275 amino acids of SEQ ID NO:2. In another embodiment, a TALL-1 protein comprises an amino acid sequence that is at least about 50%, and more preferably, at least about 60%, and more preferably, at least about 70%, and more preferably at least about 80%, and more preferably at least about 90%, and even more preferably at least about 95% identical to SEQ ID NO:2 over positions 134–285 of SEQ ID NO:2.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389–3402, incorporated herein by reference in its entirety); (2) a BLAST 2 alignment (using the parameters described below); or (3) both BLAST 2.0 and BLAST 2. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. Therefore, it is to be understood that percent identity can be determined by using either one or both of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174:247–250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalites
gap x_dropoff (50) expect (10) word size (3) filter (on).

In one embodiment of the present invention, a TALL-1 homologue is less than 100% identical to SEQ ID NO:2. In another embodiment, a TALL-1 homologue is less than about 95% identical to SEQ ID NO:2, and in another embodiment, is less than about 90% identical to SEQ ID NO:2, and in another embodiment, is less than about 80% identical to SEQ ID NO:2, and in another embodiment, is less than about 70% identical to SEQ ID NO:2, and in another embodiment, is less than about 60% identical to SEQ ID NO:2, and in another embodiment, is less than about 50% identical to SEQ ID NO:2.

A TALL-1 protein can also include proteins having an amino acid sequence comprising at least 30 contiguous amino acid residues of SEQ ID NO:2, (i.e., 30 contiguous amino acid residues having 100% identity with 30 contiguous amino acids of SEQ ID NO:2). In a preferred embodiment, a homologue of a TALL-1 amino acid sequence includes amino acid sequences comprising at least 50, and more preferably at least 75, and more preferably at least 100, and more preferably at least 115, and more preferably at least 130, and more preferably at least 150, and more preferably at least 200, and even more preferably, at least 250, contiguous amino acid residues of SEQ ID NO:2. A TALL-1 protein homologue can include proteins encoded by a nucleic acid sequence comprising at least 90, and preferably at least 150, and more preferably at least 225, and more preferably at least 300, and more preferably at least 345, and more preferably at least 390, and more preferably at least 450, and more preferably at least 600, and even more preferably at least 750, contiguous nucleotides of SEQ ID NO:1. In a preferred embodiment, a TALL-1 protein homologue has measurable TALL-1 biological activity (i.e., has biological activity).

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, a TALL-1 protein, including a TALL-1 protein homologue, includes a protein having an amino acid sequence that is sufficiently similar to a natural TALL-1 amino acid sequence that a nucleic acid sequence encoding the homologue is capable of hybridizing under low, moderate or high stringency conditions (described below) to (i.e., with) a nucleic acid molecule encoding the natural TALL-1 protein (i.e., to the complement of the nucleic acid strand encoding the natural TALL-1 amino acid sequence). Preferably, a homologue of a TALL-1 protein is encoded by a nucleic acid molecule comprising a nucleic acid sequence that hybridizes under low, moderate, or high stringency conditions to the complement of a nucleic acid sequence that encodes a protein comprising an amino acid sequence represented by SEQ ID NO:2. Even more preferably, a homologue of a TALL-1 protein is encoded by a nucleic acid molecule comprising a nucleic acid sequence that hybridizes under low, moderate, or high stringency conditions to the complement of SEQ ID NO:1. Such hybridization conditions are described in detail below. A nucleic acid sequence complement of nucleic acid sequence encoding a TALL-1 protein of the present invention refers to the nucleic acid sequence of the nucleic acid strand that is complementary to the strand which encodes TALL-1. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes the amino acid sequence SEQ ID NO:2, and/or with the complement of the nucleic acid sequence that encodes an amino acid sequence SEQ ID NO:2. Methods to deduce a complementary sequence are known to those skilled in the art. It should be noted that since amino acid sequencing and nucleic acid sequencing technologies are not entirely error-free, the sequences presented herein, at best, represent apparent sequences of a TALL-1 protein of the present invention.

TALL-1 protein homologues can be the result of natural allelic variation or natural mutation. TALL-1 protein homologues of the present invention can also be produced using techniques known in the art including, but not limited to, direct modifications to the protein or modifications to the gene encoding the protein using, for example, classic or recombinant DNA techniques to effect random or targeted mutagenesis. A naturally occurring allelic variant of a nucleic acid encoding TALL-1 is a gene that occurs at essentially the same locus (or loci) in the genome as the gene which encodes an amino acid sequence SEQ ID NO:2, but which, due to natural variations caused by, for example, mutation or recombination, has a similar but not identical sequence. Natural allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art and would be expected to be found within a given bacterial species since the genome is haploid and/or among a group of two or more bacterial species.

TALL-1 proteins also include expression products of gene fusions (for example, used to overexpress soluble, active forms of the recombinant protein), of mutagenized genes (such as genes having codon modifications to enhance gene transcription and translation), and of truncated genes (such as genes having membrane binding domains removed to generate soluble forms of a membrane protein, or genes having signal sequences removed which are poorly tolerated in a particular recombinant host). It is noted that TALL-1 proteins and protein homologues of the present invention include proteins which do not have TALL-1 activity. Such proteins are useful, for example, for the production of antibodies and for diagnostic assays.

An isolated TALL-1 protein of the present invention, including full-length proteins, truncated proteins, other homologues, and fusion proteins, can be identified in a straight-forward manner: (1) by the protein's ability to: bind to a TALL-1 receptor; costimulate B lymphocyte proliferation; costimulate B lymphocyte activation; and/or support B lymphocyte survival such as is illustrated in the Examples; (2) by the biochemical properties of the protein (e.g., molecular weight, tertiary structure, primary structure); (3) by the protein's selective binding to an antibody against a TALL-1 protein; and/or (4) by homology of the protein with other TALL-1 amino acid and nucleic acid sequences such as to TALL-1 amino acid and nucleic acid sequence from other proteins. The minimum size of a protein and/or homologue of the present invention is a size sufficient to have TALL-1 biological activity or, when the protein is not required to have such activity, sufficient to be useful for another purpose associated with a TALL-1 protein of the present invention, such as for the production of antibodies that bind to a naturally occurring TALL-1 protein. As such, the minimum size of a TALL-1 protein or homologue of the present invention is a size suitable to form at least one epitope that can be recognized by an antibody, and is typically at least 8 to 30 amino acids in length, with preferred sizes depending on whether full-length, multivalent (i.e., fusion protein having more than one domain each of which has a function), or functional portions of such proteins are desired. There is no limit, other than a practical limit, on the maximum size of such a protein in that the protein can include a portion of a TALL-1 protein (including TALL-1 homologues) or a full-length TALL-1.

Similarly, the minimum size of a nucleic acid molecule of the present invention is a size sufficient to encode a protein having TALL-1 biological activity, sufficient to encode a TALL-1 protein comprising at least one epitope which binds to an antibody, or sufficient to form a probe or oligonucleotide primer that is capable of forming a stable hybrid with the complementary sequence of a nucleic acid molecule encoding a natural TALL-1 protein (e.g., under low, moderate or high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a TALL-1 encoding sequence, a nucleic acid sequence encoding a full-length TALL-1 protein (including a TALL-1 gene), or multiple genes, or portions thereof.

The present invention also includes a fusion protein that includes a TALL-1-containing domain (including a homologue of a TALL-1 protein) attached to one or more fusion segments. Suitable fusion segments for use with the present invention include, but are not limited to, segments that can: enhance a protein's stability; provide other desirable biological activity (e.g., a cytokine); and/or assist with the purification of a TALL-1 protein (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the TALL-1-containing domain of the protein and can be susceptible to cleavage in order to enable straight-forward recovery of a TALL-1 protein. Fusion proteins are preferably produced by culturing a recombinant cell transfected with a fusion nucleic acid molecule that encodes a protein including the fusion segment attached to either the carboxyl and/or amino terminal end of a TALL-1-containing domain.

The present invention also includes a mimetic of a TALL-1 protein. As used herein, the term "mimetic" is used to refer to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example.

Such mimetics can be designed, selected and/or otherwise identified using a variety of methods known in the art. Various methods of drug design, useful to design mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety. A TALL-1 mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

According to the present invention, TALL-1 proteins can be derived from any animal, and particularly, from any animal in the Vertebrate class, Mammalia. Preferred TALL-1 proteins include isolated TALL-1 proteins from human, mouse, rat, cow, pig, baboon, and other primates. A particularly preferred isolated TALL-1 protein is a human TALL-1 protein. TALL-1 proteins from different mammalian organisms share significant homology with each other. For example, the amino acid sequence for murine TALL-1 (GenBank Accession No. AAD22475) is 56% identical (using BLAST 2 alignment, 0BLOSUM62 matrix, described below) to the amino acid sequence for human TALL-1 (SEQ ID NO:2).

Further embodiments of the present invention include nucleic acid molecules that encode a TALL-1 protein. A nucleic acid molecule of the present invention includes a nucleic acid molecule comprising a nucleic acid sequence encoding any of the isolated TALL-1 proteins, including a TALL-1 homologue, described above. A preferred Tall-1 nucleic acid molecule of the present invention includes a nucleic acid molecule comprising a nucleic acid sequence encoding a protein having an amino acid sequence comprising at least 50 contiguous amino acid residues of SEQ ID NO:2, and preferably at least 75, and more preferably at least 100, and more preferably at least 115, and more preferably at least 130, and preferably at least 150, and more preferably at least 175, and more preferably at least 200, and more preferably at least 225, and even more preferably at least 250, contiguous amino acid residues of SEQ ID NO:2. In another embodiment, a preferred Tall-1 nucleic acid molecule comprises a nucleic acid sequence comprising at least 150, and preferably at least 225, and more preferably at least 300, and more preferably at least 345, and more preferably at least 390, and more preferably at least 450, and more preferably at least 525, and more preferably at least 600, and more preferably at least 675, and even more preferably at least 750, contiguous nucleotides of SEQ ID NO:1.

In one embodiment, such nucleic acid molecules include isolated nucleic acid molecules that hybridize under low stringency conditions, and more preferably under moderate stringency conditions, and even more preferably under high stringency conditions, and even more preferably under very high stringency conditions with the complement of a nucleic acid sequence encoding a naturally occurring TALL-1 (i.e., including naturally occurring allelic variants encoding a TALL-1). Preferably, an isolated nucleic acid molecule encoding a TALL-1 protein of the present invention comprises a nucleic acid sequence that hybridizes under low, moderate, or high stringency conditions to the complement of a nucleic acid sequence that encodes a protein comprising an amino acid sequence represented by SEQ ID NO:2. In one embodiment, an isolated nucleic acid molecule comprises a nucleic acid sequence that hybridizes under low, moderate, high or very high stringency conditions to the complement of a nucleic acid sequence represented by SEQ ID NO:1.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety.

More particularly, low stringency hybridization and washing conditions, as referred to herein, refer to conditions which permit isolation of nucleic acid molecules having at least about 40% nucleic acid sequence identity with the nucleic acid molecule being used to probe in the hybridization reaction (i.e., conditions permitting about 60% or less mismatch of nucleotides). Moderate stringency hybridization and washing conditions, as referred to herein, refer to conditions which permit isolation of nucleic acid molecules having at least about 60% nucleic acid sequence identity with the nucleic acid molecule being used to probe in the hybridization reaction (i.e., conditions permitting about 40% or less mismatch of nucleotides). High stringency hybridization and washing conditions, as referred to herein, refer to conditions which permit isolation of nucleic acid molecules having at least about 75% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62.

In one embodiment of the present invention, a nucleic acid molecule encoding a TALL-1 protein of the present invention comprises a nucleic acid sequence that encodes an amino acid sequence that is at least about 40% identical to SEQ ID NO:2 over at least 175 amino acids of SEQ ID NO:2. In another embodiment, a nucleic acid molecule encoding a TALL-1 protein of the present invention comprises a nucleic acid sequence that encodes an amino acid sequence that is at least about 40% identical to SEQ ID NO:2 over positions 134–285 of SEQ ID NO:2. In this embodiment, the nucleic acid molecule is preferably a part of a recombinant nucleic acid molecule. Such a recombinant nucleic acid molecule comprises an expression vector operatively linked to the nucleic acid molecule. Recombinant nucleic acid molecules are described in detail below. In this embodiment, the TALL-1 protein preferably has TALL-1 biological activity. In this embodiment, a nucleic acid molecule encoding a TALL-1 protein of the present invention more preferably comprises a nucleic acid sequence that encodes an amino acid sequence that is at least about 50%, and more preferably, at least about 60%, and more preferably at least about 70%, and more preferably at least about 80%, and more preferably at least about 90%, and even more preferably at least about 95% identical to SEQ ID NO:2 over at least 175 amino acids of SEQ ID NO:2, and more preferably over at least about 200 amino acids, and more preferably over at least about 225 amino acids, and more preferably over at least about 250 amino acids, and even more preferably over 275 amino acids and even more preferably over the full length of SEQ ID NO:2. In another embodiment, a nucleic acid molecule encoding a TALL-1 protein of the present invention comprises a nucleic acid sequence that encodes an amino acid sequence that is at least about 50%, and more preferably, at least about 60%, and more preferably at least about 70%, and more preferably at least about 80%, and more preferably at least about 90%, and even more preferably at least about 95% identical to positions 134–285 of SEQ ID NO:2. Such a nucleic acid sequence can include a nucleic acid sequence encoding a TALL-1 protein homologue, and can therefore be referred to as a homologue of a nucleic acid sequence encoding a naturally occurring TALL-1 (i.e., a nucleic acid sequence homologue).

In another embodiment, preferred TALL-1 nucleic acid molecules of the present invention include nucleic acid molecules which comprise a nucleic acid sequence having at least about 40%, and more preferably at least about 45%, and more preferably at least about 55%, and more preferably, at least about 65%, and more preferably, at least about 75%, and even more preferably, at least about 85%, and most preferably, at least about 95% identity with a nucleic acid sequence represented by SEQ ID NO:1. Preferred TALL-1 nucleic acid molecules of the present invention also include: nucleic acid molecules which comprise a nucleic acid sequence encoding a protein comprising an amino acid sequence represented by SEQ ID NO:2 or positions 134–285 of SEQ ID NO:2; or a nucleic acid molecule comprising a nucleic acid sequence represented by SEQ ID NO:1 or positions 402–855 of SEQ ID NO:1. Percent identity is determined using BLAST 2.0 Basic BLAST default parameters, as described above.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. An isolated Tall-1 nucleic acid molecule of the present invention can be isolated from its natural source or produced using recombinant DNA technology (e.g., polymerase chain reaction (PCR) amplification, cloning) or chemical synthesis. Isolated Tall-1 nucleic acid molecules can include, for example, Tall-1 genes, natural allelic variants of Tall-1 genes, Tall-1 coding regions or portions thereof, and Tall-1 coding and/or regulatory regions modified by nucleotide insertions, deletions, substitutions, and/or inversions in a manner such that the modifications do not substantially interfere with the nucleic acid molecule's ability to encode a TALL-1 protein of the present invention or to form stable hybrids under stringent conditions with natural gene isolates. An isolated Tall-1 nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a TALL-1 protein of the present invention can vary due to degeneracies. It is noted that an isolated Tall-1 nucleic acid molecule of the present invention is not required to encode a protein having TALL-1 activity. A Tall-1 nucleic acid molecule can encode a truncated, mutated or inactive protein, for example. Such nucleic acid molecules and the proteins encoded by such nucleic acid molecules are useful in diagnostic assays, for example, or for other purposes such as antibody production. As discussed below, antibodies against TALL-1 are useful in a composition and method of the present invention.

According to the present invention, reference to a Tall-1 gene includes all nucleic acid sequences related to a natural (i.e. wild-type) Tall-1 gene, such as regulatory regions that control production of the TALL-1 protein encoded by that gene (such as, but not limited to, transcription, translation or post-translation control regions) as well as the coding region itself In another embodiment, an Tall-1 gene can be a naturally occurring allelic variant that includes a similar but not identical sequence to the nucleic acid sequence encoding a given TALL-1 protein. Allelic variants have been previously described above. The phrases "nucleic acid molecule" and "gene" can be used interchangeably when the nucleic acid molecule comprises a gene as described above.

A Tall-1 nucleic acid molecule homologue (i.e., encoding a TALL-1 protein homologue) can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Another method for modifying a recombinant nucleic acid molecule encoding a TALL-1 protein is gene shuffling (i.e., molecular breeding) (See, for example, U.S. Pat. No. 5,605,793 to Stemmer; Minshull and Stemmer; 1999, *Curr. Opin. Chem. Biol.* 3:284–290; Stemmer, 1994, *P.N.A.S. USA* 91:10747–10751, all of which are incorporated herein by reference in their entirety). This technique can be used to efficiently introduce multiple simultaneous positive changes in the TALL-1 protein action. Nucleic acid molecule homologues can be selected by hybridization with a Tall-1 gene or by screening the function of a protein encoded by a nucleic acid molecule (e.g., ability to increase B cell proliferation).

One embodiment of the present invention includes a recombinant nucleic acid molecule, which includes at least one isolated nucleic acid molecule of the present invention inserted into any nucleic acid vector (e.g., a recombinant vector) which is suitable for cloning, sequencing, and/or otherwise manipulating the nucleic acid molecule, such as expressing and/or delivering the nucleic acid molecule into a host cell to form a recombinant cell. Such a vector contains heterologous nucleic acid sequences, that is nucleic acid sequences that are not naturally found adjacent to nucleic acid molecules of the present invention, although the vector can also contain regulatory nucleic acid sequences (e.g., promoters, untranslated regions) which are naturally found adjacent to nucleic acid molecules of the present invention (discussed in detail below). The vector can be either RNA or DNA, either prokaryotic or eukaryotic, and typically is a virus or a plasmid. The vector can be maintained as an extrachromosomal element (e.g., a plasmid) or it can be integrated into the chromosome. The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome.

Typically, a recombinant molecule includes a nucleic acid molecule of the present invention operatively linked to one or more transcription control sequences. As used herein, the phrase "recombinant molecule" or "recombinant nucleic acid molecule" primarily refers to a nucleic acid molecule or nucleic acid sequence operatively linked to a transcription control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to a transcription control sequence in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in at least one of the recombinant cells useful for expressing a TALL-1 protein of the present invention. A variety of such transcription control sequences are known to those skilled in the art. Preferred transcription control sequences include those which function in bacterial, fungal (e.g., yeast), insect, plant or animal cells, and particularly, in mammalian cells including, but not limited to, monocytes or macrophages.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed TALL-1 protein to be secreted from the cell that produces the protein. Suitable signal segments include a signal segment that is naturally associated with a TALL-1 protein of the present invention or any heterologous signal segment capable of directing the secretion of a TALL-1 protein according to the present invention. In another embodiment, a recombinant molecule of the present invention comprises a leader sequence to enable an expressed TALL-1 protein to be delivered to and inserted into the membrane of a host cell. Suitable leader sequences include a leader sequence that is naturally associated with a TALL-1 protein of the present invention, or any heterologous leader sequence capable of directing the delivery and insertion of a TALL-1 protein to the membrane of a cell.

One type of recombinant molecule, referred to herein as a recombinant virus, includes a recombinant nucleic acid molecule of the present invention that is packaged in a viral coat and that can be expressed in a cell after delivery of the virus to the cell. A number of recombinant virus particles can be used, including, but not limited to, those based on alphaviruses, baculoviruses, poxviruses, adenoviruses, herpesviruses, and retroviruses.

One or more recombinant molecules of the present invention can be used to produce an encoded product (e.g., a TALL-1 protein) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one nucleic acid molecule. Preferred host cells for use in the present invention include any microorganism cell which is suitable for expression of a TALL-1 protein of the present invention, including, but not limited to, bacterial cells including, but not limited to *Escherichia coli*, and macrophages or monocytes from any species of animal.

According to the present invention, the term "transfection" is used to refer to any method by which an exogenous nucleic acid molecule (i.e., a recombinant nucleic acid molecule) can be inserted into the cell. The term "transformation" can be used interchangeably with the term "transfection" when such term is used to refer to the introduction of nucleic acid molecules into microbial cells, such as bacteria and yeast. In microbial systems, the term "transformation" is used to describe an inherited change due to the acquisition of exogenous nucleic acids by the microorganism and is essentially synonymous with the term "transfection". However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass both transfection of animal cells and transformation of microbial cells, to the extent that the terms pertain to the introduction of exogenous nucleic acids into a cell. Therefore, transfection techniques include, but are not limited to, transformation, electroporation, microinjection, lipofection, adsorption, infection and protoplast fusion.

In one embodiment, an isolated TALL-1 protein of the present invention is produced by culturing a cell that expresses the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a TALL-1 protein of the present invention. Such medium typically comprises an aqueous medium having assimilable carbon, nitrogen and phosphate sources, and appropriate salts, minerals, metals and other nutrients, such as vitamins. Examples of suitable media and culture conditions are discussed in detail in the Examples section. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the culture medium; be secreted into a space between two cellular membranes, such as the periplasmic space in *E. coli*; or be retained on the outer surface of a cell or viral membrane. The phrase "recovering the protein" refers to collecting the whole culture medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a biocatalyst or other reagent.

The present invention also includes isolated (i.e., removed from their natural milieu) antibodies capable of selectively binding to a TALL-1 protein of the present invention or a mimetic thereof (e.g., TALL-1 antibodies). As used herein, the term "selectively binds to" refers to the ability of antibodies of the present invention to preferentially bind to specified proteins and mimetics thereof of the present invention. Binding can be measured using a variety of methods standard in the art including enzyme immunoassays (e.g., ELISA), immunoblot assays, etc.; see, for example, Sambrook et al., ibid. In one embodiment, a TALL-1 antibody preferably selectively binds to a TALL-1 protein in such a way as to reduce the activity of that protein, such as by blocking the ability of the protein to bind to its receptor (i.e., a TALL-1 receptor). Isolated antibodies of the present invention can include serum containing such antibodies, or antibodies that have been purified to varying degrees. Antibodies of the present invention can be polyclonal or monoclonal, functional equivalents such as antibody fragments and genetically-engineered antibodies, including single chain antibodies or chimeric antibodies, including bi-specific antibodies that can bind to more than one epitope. A TALL-1 antibody is described in the Examples section (see Example 1).

A preferred method to produce antibodies of the present invention includes (a) administering to an animal an effective amount of a protein, peptide or mimetic thereof of the present invention to produce the antibodies and (b) recovering the antibodies. In another method, antibodies of the present invention are produced recombinantly using techniques as heretofore disclosed to produce TALL-1 proteins of the present invention. Antibodies raised against defined proteins or mimetics can be advantageous because such antibodies are not substantially contaminated with antibodies against other substances that might otherwise cause interference in a diagnostic assay or side effects if used in a therapeutic composition.

As discussed above, the present inventors have discovered that the receptor for TALL-1 is a protein called B cell maturation factor (BCMA, primarily referred to herein as the TALL-1 receptor). A nucleic acid molecule encoding human BCMA (TALL-1 receptor) is identified as GenBank Accession No. U95742, and the human BCMA (TALL-1 receptor) protein is identified under GenBank Accession No. AAB6725 1 or SwissProt Accession No. Q02223. A nucleic acid molecule comprising a nucleic acid sequence encoding human BCMA (TALL-1 receptor) is also represented herein as SEQ ID NO:10, with the coding region spanning from nucleotide positions 67–621 of SEQ ID NO:10. SEQ ID NO:10 encodes a 184 amino acid BCMA (TALL-1 receptor) protein represented herein as SEQ ID NO:11. A nucleic acid molecule encoding murine BCMA (TALL-1 receptor) is identified as GenBank Accession No. AF061505, and the murine BCMA (TALL-1 receptor) protein is identified under GenBank Accession No. AAC23799. A nucleic acid molecule comprising a nucleic acid sequence encoding murine BCMA (TALL-1 receptor) is also represented herein as SEQ ID NO:16. SEQ ID NO:16 encodes a 185 amino acid BCMA (TALL-1 receptor) protein represented herein as SEQ ID NO:17. According to the present invention, reference to a TALL-1 receptor includes full-length TALL-1 receptor proteins, fusion proteins, or any homologue of such a protein.

Knowing the identity of the receptor for TALL-1 allows one of skill in the art to modify the receptor in a manner that the ability of the receptor to interact with TALL-1 and be activated by TALL-1 can be regulated. Therefore, yet another embodiment of the present invention relates to an isolated TALL-1 receptor homologue, wherein said homologue comprises an amino acid sequence that is: (a) at least about 40% identical to SEQ ID NO:11 over at least 35 amino acids of SEQ ID NO:11; and, (b) less than 100% identical to an amino acid sequence selected from the group of SEQ ID NO:11 and SEQ ID NO:17. According to the present invention, a homologue of a TALL-1 receptor (i.e., a TALL-1 receptor homologue) includes TALL-1 receptors in which at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol).

Preferably, an isolated TALL-1 receptor homologue of the present invention has TALL-1 receptor biological activity. TALL-1 biological activity can include, but is not limited to: TALL-1 receptor transcription, TALL-1 receptor translation, TALL-1 receptor phosphorylation, binding to TALL-1, receptor translocation within a cell, NFκB activation, TRAF5, TRAF6, NIK, IKKα and/or IKKβ activation, costimulation of B cell proliferation, costimulation of B cell activation, and enhancement of B cell survival. Such activities and methods of detecting the same are described in the Examples section and/or are known in the art, given the guidance provided herein.

Preferably, an isolated TALL-1 receptor homologue of the present invention is at least about 45% identical to SEQ ID NO:11 over at least 35 amino acids of SEQ ID NO:11, and more preferably at least about 50% identical, and more preferably at least about 55% identical, and more preferably at least about 60% identical, and even more preferably at least about 65% identical, and even more preferably at least about 70% identical, and even more preferably at least about 75% identical and even more preferably at least about 80% identical, and even more preferably at least about 85% identical, and even more preferably at least about 90% identical to SEQ ID NO:11 over at least about 35 amino acids, and more preferably at least 50 amino acids, and more preferably at least 75 amino acids and more preferably at least 100 amino acids, and more preferably at least 125 amino acids, and more preferably at least 150 amino acids, and even more preferably at least 175 amino acids, and even more preferably, over the full-length of SEQ ID NO:11.

As discussed above, a TALL-1 receptor homologue is less than 100% identical to SEQ ID NO:11 and SEQ ID NO:17. In one embodiment, a TALL-1 receptor homologue is less than about 95% identical to SEQ ID NO:11 and SEQ ID NO:17, and in another embodiment, is less than about 90% identical to SEQ ID NO:11 and SEQ ID NO:17, and in another embodiment, is less than about 80% identical to SEQ ID NO:11 and SEQ ID NO:17, and in another embodiment, is less than about 70% identical to SEQ ID NO:11 and SEQ ID NO:17, and in another embodiment, is less than about 60% identical to SEQ ID NO:11 and SEQ ID NO:17, and in another embodiment, is less than about 50% identical to SEQ ID NO:11 and SEQ ID NO:17.

In one embodiment, such a TALL-1 receptor homologue is encoded by a nucleic acid molecule comprising a nucleic acid sequence that hybridizes under moderate stringency conditions to the complement of SEQ ID NO:10. In another embodiment, such a TALL-1 receptor homologue is encoded by a nucleic acid molecule comprising a nucleic acid sequence that hybridizes under high stringency conditions to the complement of SEQ ID NO:10. Hybridization conditions have been discussed in detail with regard to the TALL-1 protein above and are the same with regard to a TALL-1 receptor homologue.

In one embodiment, a TALL-1 receptor homologue is a soluble TALL-1 receptor, such as the soluble TALL-1 receptor described in the Examples section. In another embodiment, a TALL-1 receptor homologue binds to TALL-1, and in one aspect of this embodiment, such a TALL-1 receptor homologue is not activated by the binding of TALL-1 as would be a wild-type TALL-1 receptor. In another embodiment, a TALL-1 receptor homologue does not bind to TALL-1, or binds with less affinity to TALL-1 as compared to the wild-type receptor. In yet another embodiment, the TALL-1 receptor homologue activates NF-κB in a cell expressing the homologue (e.g., a B lymphocyte) through a TRAF5, TRAF6, NIK, IKKα and IKKβ dependent pathway. In another embodiment, the TALL-1 receptor homologue costimulates B lymphocyte proliferation in a B lymphocyte expressing the homologue.

The present invention also includes a fusion protein that includes a TALL-1 receptor-containing domain (including a homologue of a TALL-1 receptor) attached to one or more fusion segments. Suitable fusion segments for use with the present invention include, but are not limited to, segments that can: enhance a protein's stability; provide other desirable biological activity (e.g., a cytokine); and/or assist with the purification of a TALL-1 receptor (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the TALL-1 receptor-containing domain of the protein and can be susceptible to cleavage in order to enable straightforward recovery of a TALL-1 receptor. Fusion proteins are preferably produced by culturing a recombinant cell transfected with a fusion nucleic acid molecule that encodes a protein including the fusion segment attached to either the carboxyl and/or amino terminal end of a TALL-1 receptor-containing domain.

The present invention also includes a mimetic of a TALL-1 receptor. The term "mimetic" has been defined above. TALL-1 receptor mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example.

Yet another embodiment of the present invention relates to an isolated nucleic acid molecule comprising a nucleic acid sequence encoding any of the above-identified TALL-1 receptor homologues. In one embodiment, the nucleic acid sequence encodes a homologue comprising an amino acid sequence that is: (a) at least about 40% identical to SEQ ID NO:11 over at least 35 amino acids of SEQ ID NO:11; and/or, (b) less than 100% identical to an amino acid sequence selected from the group consisting of SEQ ID NO:11 and SEQ ID NO:17. Also included in the present invention are recombinant nucleic acid molecules, recombinant viruses and recombinant cells comprising such a nucleic acid molecule. Recombinant nucleic acid molecules, viruses, and cells have been described in detail above with regard to TALL-1 proteins and that discussion is applied here to recombinant nucleic acid molecules, viruses and cells comprising nucleic acid molecules encoding TALL-1 receptor homologues.

Also included in the present invention is a method to produce a TALL-1 receptor homologue, comprising expressing a nucleic acid molecule as described herein under conditions effective to produce the homologue. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one nucleic acid molecule. Preferred host cells for use in the present invention include any microorganism cell which is suitable for expression of a TALL-1 receptor protein of the present invention, including, but not limited to, bacterial cells including, but not limited to *Escherichia coli*, and B lymphocytes from any species of animal.

Yet another embodiment of the present invention relates to an isolated antibody that selectively binds to a TALL-1 receptor, including a TALL-1 receptor homologues and mimetics. In one embodiment, a TALL-1 receptor antibody preferably selectively binds to a TALL-1 receptor in such a way as to reduce the activity of that protein, such as by blocking the ability of the receptor to bind to its ligand (i.e., a TALL-1 protein). Isolated antibodies of the present invention can include serum containing such antibodies, or antibodies that have been purified to varying degrees. Antibodies of the present invention can be polyclonal or monoclonal, functional equivalents such as antibody fragments and genetically-engineered antibodies, including single chain antibodies or chimeric antibodies, including bi-specific antibodies that can bind to more than one epitope.

Having described TALL-1 proteins and TALL-1 receptors in detail, various aspects of the present invention related to the use of TALL-1 and its receptor will be described. One such embodiment of the present invention relates to a composition comprising: (a) a compound selected from the group consisting of: (i) an isolated TALL-1 protein; (ii) an isolated antibody that specifically binds to a TALL-1 protein of(i); (iii) an isolated TALL-1 receptor; and, (iv) an isolated antibody that specifically binds to a TALL-1 receptor of (iii); and, (b) a pharmaceutically acceptable carrier. In this aspect of the present invention, an isolated TALL-1 protein can be any of the TALL-1 proteins previously described herein, including, but not limited to, a wild-type TALL-1 protein, a TALL-1 protein homologue, a soluble TALL-1 protein, and/or a TALL-1 fusion protein. Similarly, an isolated TALL-1 receptor can be any of the TALL-1 receptor proteins previously described herein, including, but not limited to, a wild-type TALL-1 receptor, a TALL-1 receptor homologue, a soluble TALL-1 receptor, and/or a TALL-1 receptor fusion protein. An isolated antibody that selectively binds to a TALL-1 protein or a TALL-1 receptor has also been described above. In one embodiment, a composition of the present invention can include nucleic acid molecules encoding TALL-1 and/or a TALL-1 receptor, and/or a mimetic of TALL-1 or a TALL-1 receptor. In one embodiment, a composition of the present invention includes a combination of at least two of any of the above-identified compounds.

Compositions of the present invention are useful for regulating biological processes mediated by monocytes, macrophages, B lymphocytes, and/or interactions between B lymphocytes and monocytes or macrophages. In particular, compositions of the present invention are useful for regulating the interaction between TALL-1 and its receptor (TALL-1 receptor or BCMA). In some embodiments, such compositions are useful for increasing (e.g., costimulating, enhancing, upregulating) the interaction between TALL-1 and its receptor. In this embodiment, the composition is used, for example, in a method to activate a TALL-1 receptor, or more particularly, to increase B lymphocyte proliferation, to increase B lymphocyte activation, or to increase B lymphocyte survival. Such methods, described in detail below, are especially useful to enhance vaccination protocols, to treat patients in which B lymphocyte proliferation, activation or survival is inadequate, or to enhance B lymphocyte proliferation, activation or survival in an in vitro assay.

In some embodiments, such compositions are useful for decreasing (e.g., inhibiting, reducing, downregulating) the interaction between TALL-1 and its receptor. In this embodiment, the composition is used, for example, in a method to inhibit activation of a TALL-1 receptor, or more particularly, to decrease B lymphocyte proliferation, to decrease B lymphocyte activation, or to decrease B lymphocyte survival. Such methods, also described in detail below, are especially useful to treat patients in which inhibition of B lymphocyte proliferation, activation and/or survival is beneficial. Specifically, such methods are useful for treating patients with an autoimmune disease, and particularly an autoimmune disease in which B lymphocyte proliferation, activation or survival is problematic. Such autoimmune diseases include, but are not limited to, rheumatoid arthritis, systemic lupus erythematosus, insulin dependent diabetes mellitis, multiple sclerosis, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, or polyarteritis nodosa.

According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably a monocyte or macrophage, when TALL-1 is the target molecule (i.e., the molecule which is to be regulated or otherwise targeted by the composition), and a B lymphocyte, when TALL-1 receptor is the target. In some embodiments, a suitable site for delivery is a site of interaction between B lymphocytes and monocytes or macrophages. Preferred pharmaceutically acceptable carriers are capable of maintaining a protein, compound, or recombinant nucleic acid molecule of the present invention in a form that, upon arrival of the protein, compound, or recombinant nucleic acid molecule at the cell target in a culture or in patient, the protein, compound or recombinant nucleic acid molecule is capable of interacting with its target (e.g., a naturally occurring TALL-1 protein, including membrane and/or soluble TALL-1 proteins, or a TALL-1 receptor).

Suitable excipients of the present invention include excipients or formularies that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal,—or o-cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a compound of the present invention (e.g., a protein (including homologues), an antibody, a nucleic acid molecule, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposhperes, and transdermal delivery systems. Other carriers of the present invention include liquids that, upon administration to a patient, form a solid or a gel in situ. Preferred carriers are also biodegradable (i.e., bioerodible). When the compound is a recombinant nucleic acid molecule, suitable delivery vehicles include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of a compound of the present invention at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles poly-L-lysine/DNA-molecular conjugates, and artificial chromosomes.

A pharmaceutically acceptable carrier which is capable of targeting is herein referred to as a "delivery vehicle." Delivery vehicles of the present invention are capable of delivering a composition of the present invention to a target site in a patient. A "target site" refers to a site in a patient to which one desires to deliver a composition. For example, a target site can be any cell which is targeted by direct injection or delivery using liposomes, viral vectors or other delivery vehicles, including ribozymes. Examples of delivery vehicles include, but are not limited to, artificial and natural lipid-containing delivery vehicles, viral vectors, and ribozymes. Natural lipid-containing delivery vehicles include cells and cellular membranes. Artificial lipid-containing delivery vehicles include liposomes and micelles. A delivery vehicle of the present invention can be modified to target to a particular site in a mammal, thereby targeting and making use of a compound of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One preferred delivery vehicle of the present invention is a liposome. A liposome is capable of remaining stable in an animal for a sufficient amount of time to deliver a nucleic acid molecule described in the present invention to a preferred site in the animal. A liposome, according to the present invention, comprises a lipid composition that is capable of delivering a nucleic acid molecule described in the present invention to a particular, or selected, site in a patient. A liposome according to the present invention comprises a lipid composition that is capable of fusing with the plasma membrane of the targeted cell to deliver a nucleic acid molecule into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule of the present invention can be achieved using methods standard in the art.

Another preferred delivery vehicle comprises a viral vector. A viral vector includes an isolated nucleic acid molecule useful in the present invention, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

A composition of the present invention can be delivered to a cell culture or patient by any suitable method. Selection of such a method will vary with the type of compound being administered or delivered (i.e., protein, nucleic acid, mimetic), the mode of delivery (i.e., in vitro, in vivo, ex vivo) and the goal to be achieved by administration/delivery of the compound or composition. According to the present invention, an effective administration protocol (i.e., administering a composition in an effective manner) comprises suitable dose parameters and modes of administration that result in delivery of a composition to a desired site (i.e., to a desired cell) and/or in regulation of B lymphocyte proliferation, B lymphocyte activation and/or B lymphocyte survival in a patient. Administration routes include in vivo, in vitro and ex vivo routes. In vivo routes include, but are not limited to, oral, nasal, intratracheal injection, inhaled, transdermal, rectal, and parenteral routes. Preferred parenteral routes can include, but are not limited to, subcutaneous, intradermal, intravenous, intramuscular and intraperitoneal routes. In a preferred embodiment of the present invention, a composition containing a TALL-1 or TALL-1 receptor protein, antibody, mimetic, or nucleic acid molecule of the present invention is administered by a parenteral route. Intravenous, intraperitoneal, intradermal, subcutaneous and intramuscular administrations can be performed using methods standard in the art. Aerosol (inhalation) delivery can also be performed using methods standard in the art (see, for example, Stribling et al., *Proc. Natl. Acad. Sci. USA* 189:11277–11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Such routes can include the use of pharmaceutically acceptable carriers as described above. Ex vivo refers to performing part of the regulatory step outside of the patient, such as by transfecting a population of cells removed from a patient with a recombinant molecule comprising a nucleic acid sequence encoding a protein according to the present invention under conditions such that the recombinant molecule is subsequently expressed by the transfected cell, and returning the transfected cells to the patient. In vitro and ex vivo routes of administration of a composition to a culture of host cells can be accomplished by a method including, but not limited to, transfection, transformation, electroporation, microinjection, lipofection, adsorption, protoplast fusion, use of protein carrying agents, use of ion carrying agents, use of detergents for cell permeabilization, and simply mixing (e.g., combining) a compound in culture with a target cell.

In accordance with the present invention, a suitable single dose size is a dose that is capable of regulating B lymphocyte proliferation, activation and/or survival when administered one or more times over a suitable time period. Doses can vary depending upon the goal of the administration or the condition or the disease being treated. Preferably, a protein or antibody of the present invention is administered in an amount that is between about 50 U/kg and about 15,000 U/kg body weight of the patient. In another embodiment, a protein or antibody is administered in an amount that is between about 0.01 $\mu$g and about 10 mg per kg body weight of the patient, and more preferably, between about 0.1 $\mu$g and about 100 $\mu$g per kg body weight of the patient. When the compound to be delivered is a nucleic acid molecule, an appropriate single dose results in at least about 1 pg of protein expressed per mg of total tissue protein per $\mu$g of nucleic acid delivered. More preferably, an appropriate single dose is a dose which results in at least about 10 pg of protein expressed per mg of total tissue protein per fig of nucleic acid delivered; and even more preferably, at least about 50 pg of protein expressed per mg of total tissue protein per $\mu$g of nucleic acid delivered; and most preferably, at least about 100 pg of protein expressed per mg of total tissue protein per $\mu$g of nucleic acid delivered. A preferred single dose of a naked nucleic acid vaccine ranges from about 1 nanogram (ng) to about 100 $\mu$g, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 $\mu$m in diameter) and are propelled into skin cells or muscle with a "gene gun." It will be obvious to one of skill in the art that the number of doses administered to a patient is dependent upon the goal of the administration (e.g., the extent of the disease and the response of an individual patient to the treatment). Therefore, it is within the scope of the present invention that a suitable number of doses includes any number required to regulate B lymphocyte proliferation, activation and/or survival, or to regulate a disease or condition related thereto. Effective in vivo dose parameters can be determined using methods standard in the art. Such methods include, for example, determination of survival rates, side effects (i.e., toxicity), determination of cellular and humoral immune response effects, and/or effects on conditions related to B lymphocyte proliferation, activation and/or survival.

In the method of the present invention, TALL-1 and TALL-1 receptor proteins (including homologues), antibodies, nucleic acid molecules and/or mimetics, as well as compositions comprising such compounds can be administered to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, rabbits, sheep, cattle, horses and pigs, with humans being most preferred. According to the present invention, administration of a composition is useful to regulate a target cell. Typically, it is desirable to modulate proliferation, activation, and/or survival of a B lymphocyte to obtain a therapeutic benefit in a patient. Patients whom are suitable candidates for the method of the present invention include, but are not limited to, patients that will benefit from reduced B lymphocyte proliferation, activation and/or survival, such as patients that have, or are at risk of developing (e.g., are predisposed to), autoimmune diseases, and immunoproliferative diseases, as well as patients in need of enhanced B lymphocyte proliferation, activation or survival (e.g., patients receiving a vaccination or patients having a suppressed immune system).

Compositions of the present invention, and the compounds in such compositions, are to useful in a variety of methods which make use of the discovery that TALL-1 is the ligand for the TALL-1 (BCMA) receptor. Accordingly, one embodiment of the present invention relates to a method to activate a TALL-1 receptor, comprising contacting a TALL-1 receptor with a TALL-1 protein. In a preferred embodiment, the TALL-1 receptor is expressed by a B lymphocyte. Such method can be performed in vitro, ex vivo or in vivo. According to the present invention, reference to "B cells" or "B lymphocytes" includes splenic B cells, lymph node B cells, myeloma cells, peripheral blood B cells, bone marrow B cells and hybridoma cells. Hybridoma cells refer to hybrid cell lines comprising myeloma cells (tumor cells capable of being maintained in tissue culture but do not produce immunoglobulin) fused with, for example, a spleen cell capable of producing an immunoglobulin molecule. The TALL-1 protein can be any TALL-1 protein as previously described herein, including a wild-type TALL-1 protein (membrane or soluble), a TALL-1 homologue, a TALL-1 fusion protein, or a TALL-1 peptide mimetic. The step of contacting can be by any suitable method, including any of the methods of administration or delivery described above. Preferably, the TALL-1 receptor is contacted with the TALL-1 protein in a manner such that the TALL-1 protein can bind to the receptor, and thereby activate the receptor. TALL-1 receptor activation can be detected using any suitable method including, but not limited to, detection of increased TALL-1 receptor transcription, detection of increased TALL-1 receptor translation, detection of increased NFκB activation, detection of the activation of TRAF5, TRAF6, NIK, IKKα or IKKβ, detection of B cell proliferation, detection of B cell survival. Many of such methods are described in detail in the Examples section, and suitable methods for all such steps of detection are known in the art.

Yet another embodiment of the present invention relates to a method to regulate B lymphocyte proliferation, activation, or survival. Such a method includes the step of regulating the biological activity of a TALL-1 receptor, wherein the TALL-1 receptor is expressed by a B lymphocyte. According to the present invention, to regulate the biological activity of a TALL-1 receptor refers to upregulating (e.g., stimulating, enhancing, increasing) the biological activity of the receptor or to downregulating (e.g., decreasing, reducing, inhibiting) the biological activity of the receptor. As described above, a biological activity of a TALL-1 receptor includes, costimulation of B cell proliferation, costimulation of B cell activation, and/or enhancement of B cell survival, as well as more particular activities such as NFκB activation or activation of TRAF5, TRAF6, NIK, IKKα or IKKβ.

In one embodiment of the present invention, this method of the present invention is used to inhibit the biological activity of the TALL-1 receptor. TALL-1 receptor activity can be inhibited, for example, by inhibiting the interaction of TALL-1 with the TALL-1 receptor. Such inhibition can be achieved by any suitable means of inhibiting the interaction between TALL-1 and TALL-1 receptor including, but not limited to, downregulating expression of TALL-1 (e.g., by inhibition of macrophages or monocyte activity, by antisense methods, by ribozyme methods, etc.), downregulating expression of the TALL-1 receptor (e.g., by inhibition of B cell activity, by antisense methods, by ribosyme methods, etc.), and/or by physically blocking the interaction.

In one aspect, the step of inhibiting comprises contacting TALL-1 expressed by a monocyte or macrophage with a compound that inhibits binding of the TALL-1 to the TALL-1 receptor. Such a compound can include, but is not limited to: (a) an antibody that selectively binds to TALL-1 and inhibits the binding of TALL-1 to the TALL-1 receptor; (b) a soluble TALL-1 receptor; and, (c) a TALL-1 receptor homologue, including any of the TALL-1 receptor homologues described herein. In this aspect, a TALL-1 receptor homologue preferably binds to TALL-1, but does not activate signal transduction molecules, such as NF-κB, in a B lymphocyte, when expressed by such a cell. Such a homologue can compete with a wild-type TALL-1 receptor for the binding to TALL-1. In one embodiment, such a homologue binds to TALL-1 with a greater affinity than does the wild-type TALL-1 receptor. Such a compound can also include TALL-1 receptor mimetics that are capable of binding to TALL-1 but which do induce TALL-1 receptor biological activity.

In another aspect of this method, the step of inhibiting comprises contacting the TALL-1 receptor with a compound that inhibits the interaction of TALL-1 with the TALL-1 receptor. The TALL-1 receptor is expressed by a B lymphocyte. Such a compound can include, but is not limited to: (a) an antibody that selectively binds to the TALL-1 receptor and inhibits the binding of the TALL-1 receptor by TALL-1; and (b) a TALL-1 homologue, including any of the TALL-1 homologues described herein. Preferably, such a homologue binds to the TALL-1 receptor but does not activate the TALL-1 receptor. The compound can also include TALL-1 mimetics that are capable of binding to a TALL-1 receptor, but which do not induce TALL-1 receptor biological activity.

In some embodiments, it is desirable to regulate TALL-1 receptor activity, and thus B lymphocyte activity, by increasing the biological activity of the TALL-1 receptor. TALL-1 receptor activity can be increased, for example, by increasing the interaction of TALL-1 with the TALL-1 receptor. Such an increase can be achieved by any suitable means of upregulating the interaction between TALL-1 and TALL-1 receptor including, but not limited to, upregulating expression of TALL-1 (e.g., by stimulation of macrophages or monocyte activity), upregulating expression of the TALL-1 receptor (e.g., by stimulation of B cell activity or genetically engineering B lymphocytes to overexpress TALL-1 receptor), and/or by physically inducing or increasing the interaction between TALL-1 and TALL-1 receptor. In one embodiment, such a method includes contacting the TALL-1 receptor with a compound that increases TALL-1 receptor activity. Such a compound can include, but is not limited to: (a) an isolated TALL-1 protein; and, (b) an antibody that selectively binds to the TALL-1 receptor and activates the receptor. An isolated TALL-1 protein can include any TALL-1 protein, including TALL-1 homologues, described herein. The TALL-1 homologue binds to a TALL-1 receptor in a manner effective to activate the TALL-1 receptor, when such receptor is expressed by a B lymphocyte. Such a compound can also include TALL-1 mimetics that bind to and activate a TALL-1 receptor.

Preferably, regulation of B lymphocyte proliferation by the method is effective to regulate a B-lymphocyte immune response in an animal. For example, when upregulation of a B lymphocyte immune response is desired, such as when a patient is vaccinated, or when a patient has a suppressed B cell response due to disease or stress, the interaction between TALL-1 and TALL-1 receptor is preferably increased. When downregulation of a B lymphocyte immune response is desired, such as when a patient has an autoimmune disease, and particularly an autoimmune disease in which autoreactive B lymphocytes play a prominent role, the interaction between TALL-1 and TALL-1 receptor is preferably decreased.

According to the present invention, the method of the present invention is primarily directed to the regulation of the biological activity of a target cell (i.e., a B lymphocyte, a monocyte or a macrophage) in a patient with the added, but not required, goal of providing some therapeutic benefit to a patient. Modulating the phenotype of a target cell in a patient in the absence of obtaining some therapeutic benefit is useful for the purposes of determining factors involved (or not involved) in a disease and preparing a patient to more beneficially receive another therapeutic composition. In a preferred embodiment, however, the methods of the present invention are directed to the modulation of the phenotype of a target cell which is useful in providing some therapeutic benefit to a patient. As such, a therapeutic benefit is not necessarily a cure for a particular disease or condition, but rather, preferably encompasses a result which can include alleviation of the disease or condition, elimination of the disease or condition, reduction of a symptom associated with the disease or condition, prevention or alleviation of a secondary disease or condition resulting from the occurrence of a primary disease or condition, and/or prevention of the disease or condition. As used herein, the phrase "protected from a disease" refers to reducing the symptoms of the disease; reducing the occurrence of the disease, and/or reducing the severity of the disease. Protecting a patient can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment) to reduce the symptoms of the disease. In particular, protecting a patient from a disease or enhancing another therapy (e.g., vaccination) is accomplished by regulating the interaction between TALL-1 and TALL-1 receptor such that a beneficial effect is obtained. A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

In one embodiment, by performing the method of the present invention, the interaction between TALL-1 and TALL-1 receptor is deceased, such a decrease being sufficient to downregulate B lymphocyte proliferation, activation and/or survival in a patient (or in a culture, if the method is performed in vitro or ex vivo). In one embodiment, when the target cell is an autoreactive B lymphocyte, typically, the patient has or is at risk of developing an autoimmune disease associated with the autoreactive B lymphocyte. Such autoimmune diseases can be any autoimmune disease, and particularly include, rheumatoid arthritis, systemic lupus erythematosus, insulin dependent diabetes mellitus, multiple sclerosis, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, or polyarteritis nodosa. The autoreactive B lymphocyte in such a patient, prior to the step of administering the composition of the present invention, generally has normal or enhanced proliferation, activation, and/or survival as compared to a B lymphocyte from a patient that does not have and is not at risk of developing the autoimmune disease.

Inhibition of the interaction between TALL-1 and TALL-1 receptor expressed by an autoreactive B lymphocyte can result in a reduction in the proliferation, activation and/or survival of the B lymphocyte, which can be detected as a change in: B lymphocyte cytokine production, a reduction in NFκB activation, a reduction in TRAF5, TRAF6, NIK, IKKα and IKKβ activation, a reduction in immunoglobulin maturation, a reduction in immunoglobulin production and secretion, a reduction in calcium mobilization, or a reduction in phosphorylation of signal transduction proteins. Preferably, inhibition of the interaction between TALL-1 and TALL-1 receptor in the B lymphocytes of the patient produces a result in the patient which includes, but is not limited to, decreased autoantibody production, decreased autoreactive B cell proliferation, decreased autoreactive B cell survival, and/or reduced destruction of autologous cells or tissues, as compared to any of these measurements prior to the conducting of the method of the present invention, or as compared to a patient with the disease who has not been administered the composition of the present invention.

In one embodiment, by performing the method of the present invention, the interaction between TALL-1 and TALL-receptor is increased, such an increase being sufficient to upregulate B lymphocyte proliferation, activation and/or survival in a patient (or in a culture, if the method is performed in vitro or ex vivo). In one embodiment, the target cell is a normal B lymphocyte (e.g., in a patient receiving a vaccination), an anergic B lymphocyte, or a B lymphocyte in a patient suffering from a suppressed humoral immune response (e.g., in an immune compromised patient). The B lymphocyte in such a patient, prior to the step of administering the composition of the present invention, generally has normal or reduced proliferation, activation, and/or survival as compared to a B lymphocyte from a normal individual, to a patient who is not immune compromised, or to a patient that does not have and is not at risk of developing the disease.

Increasing the interaction between TALL-1 and TALL-1 receptor expressed by a normal or suppressed B lymphocyte can result in an increase in the proliferation, activation and/or survival of the B lymphocyte, which can be detected as a change in: B lymphocyte cytokine production, an increase in NFκB activation, an increase in TRAF5, TRAF6, NIK, IKKα and IKKβ activation, an increase in immunoglobulin maturation, an increase in immunoglobulin production and secretion, an increase in calcium mobilization, and/or an increase in phosphorylation of intracellular signal transduction proteins. Preferably, increasing the interaction between TALL-1 and TALL-1 receptor in the B lymphocytes of the patient produces a result in the patient which includes, but is not limited to, increased antibody production, increased B cell proliferation, and increased B cell survival, as compared to any of these measurements prior to the conducting of the method of the present invention, or as compared to a patient with the disease who has not been administered the composition of the present invention.

Yet another embodiment of the present invention relates to a method to identify compounds that regulate B lymphocyte proliferation, activation and/or survival by regulating the interaction between TALL-1 and a TALL-1 receptor. In one embodiment, the method can be a cell-free or a cell-based assay which includes the steps of: (a) contacting a TALL-1 receptor with a putative regulatory compound; (b) contacting the TALL-1 receptor with a TALL-1 protein; and (c) detecting whether the TALL-1 protein is capable of binding to the receptor in the presence of the putative regulatory compound as compared to in the absence of the putative regulatory compound. In another embodiment, the method includes the steps of: (a) contacting a TALL-1 protein with a putative regulatory compound; (b) contacting the TALL-1 protein with a TALL-1 receptor; and, (c) detecting whether the TALL-1 protein is capable of binding to the receptor in the presence of the putative regulatory compound as compared to in the absence of the putative regulatory compound. Preferably, step (a) is performed prior to step (b) in these embodiments. In one aspect, an additional step can be performed prior to step (b) to determine whether the putative compound regulates (binds to and/or activates) TALL-1 or TALL-1 receptor activity directly. In these embodiments, the TALL-1 protein can be soluble or otherwise cell-free (e.g., the membrane form separate from cell membranes); expressed by a cell, such as a monocyte, macrophage, or other cell capable of expressing TALL-1; or provided in a cell lysate. The TALL-1 receptor can be provided as a soluble protein or otherwise cell-free (e.g., in the absence of cell membranes); expressed by a cell, such as a B lymphocyte, or other cell capable of expressing TALL-1 receptor; or in a cell lysate.

In these embodiments, reduced binding of TALL-1 to its receptor in the presence of the putative regulatory compound as compared to in the absence of the compound indicates that the putative regulatory compound is an inhibitor of TALL-1 and TALL-1 receptor interaction. The compound can be further tested, if desired, in a cell-based assay to determine whether the compound inhibits the biological activity of the TALL-1 receptor, as determined by a reduction in TALL-1 biological activity as previously described herein. Similarly, in this embodiment, increased binding of TALL-1 to its receptor in the presence of the putative regulatory compound as compared to in the absence of the compound indicates that the putative regulator is an enhancer of TALL-1 and TALL-1 receptor interaction. If no change in the binding of TALL-1 to its receptor is detected in the presence of the putative regulatory compound as compared to in the absence of the compound, one can conclude that the compound does not appear to affect the binding of TALL-1 to its receptor. In this instance, a cell-based assay can be used to detect whether the putative regulatory compound increases or decreases the biological activity of a TALL-1 receptor.

In further embodiment of the method of the present invention, such a method is a cell-based assay which includes the steps of: (a) contacting a B lymphocyte expressing a TALL-1 receptor with a putative regulatory compound; (b) contacting the B lymphocyte with a TALL-1 protein as previously described herein; and, (c) detecting whether the putative regulatory compound regulates the TALL-1 receptor. Alternatively, the method can include the steps of: (a) contacting a macrophage or monocyte expressing a TALL-1 protein, or alternatively, contacting a TALL-1 protein in the absence of a cell (e.g., soluble TALL-1), with a putative regulatory compound; (b) contacting the TALL-1 protein (expressed by a cell or cell-free) with a TALL-1 receptor protein expressed by a B lymphocyte; and, (c) detecting whether the putative regulatory compound regulates the TALL-1 receptor. Preferably, step (a) is performed prior to step (b) in these embodiments. In one aspect, an additional step can be performed prior to step (b) to determine whether the putative compound regulates (binds to and/or activates) TALL-1 or TALL-1 receptor activity directly. In this assay, the TALL-1 protein can be soluble or otherwise cell-free (e.g., the membrane form separate from cell membranes); expressed by a cell, such as a monocyte, macrophage, or other cell capable of expressing TALL-1; or provided in a cell lysate. The TALL-1 receptor is expressed by a cell, such as a B lymphocyte, or other cell capable of expressing TALL-1 receptor.

In these embodiments, reduced binding of TALL-1 to its receptor and/or reduced TALL-1 receptor biological activity in the presence of the putative regulatory compound as compared to in the absence of the compound indicates that the putative regulatory compound is an inhibitor of TALL-1 and TALL-1 receptor interaction, and/or an inhibitor of TALL-1 receptor biological activity. Similarly, in this embodiment, increased binding of TALL-1 to its receptor and/or increased TALL-1 receptor biological activity in the presence of the putative regulatory compound as compared to in the absence of the compound indicates that the putative regulator is an enhancer of TALL-1 and TALL-1 receptor interaction and/or of TALL-1 biological activity. If no change in the binding of TALL-1 to its receptor is detected in the presence of the putative regulatory compound as compared to in the absence of the compound, one can conclude that the compound does not appear to affect the binding of TALL-1 to its receptor, although an increase or decrease in the biological activity of a TALL-1 receptor may still be detected.

As used herein, the term "putative" refers to compounds having an unknown or previously unappreciated regulatory activity in a particular process. As such, the term "identify" is intended to include all compounds, the usefulness of which as a regulatory compound of the interaction between TALL-1 and TALL-1 receptor for the purposes of regulating B lymphocyte proliferation, activation and/or survival is determined by a method of the present invention.

The methods of the present invention include contacting a TALL-1 protein and/or a TALL-1 receptor with a compound being tested for its ability to bind to TALL-1 or TALL-1 receptor and/or to regulate the activity of TALL-1 and/or its receptor, such as by blocking the interaction between the ligand and receptor. The step of contacting can be performed by any suitable method, depending on how the TALL-1 and/or TALL-1 receptor are provided. For example, cells expressing TALL-1 or TALL-1 receptor can be grown in liquid culture medium or grown on solid medium in which the liquid medium or the solid medium contains the compound to be tested. In addition, as described above, the liquid or solid medium contains components necessary for cell growth, such as assimilable carbon, nitrogen and micronutrients. Cell lysates can be combined with other cell lysates and/or the compound to be tested in any suitable medium. In another embodiment, the TALL-1 protein and/or the TALL-1 receptor and/or cell lysates containing such proteins can be immobilized on a substrate such as: artificial membranes, organic supports, biopolymer supports and inorganic supports. The protein can be immobilized on the solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports can be in any suitable form, including in a bead form, plate form, or well form.

The present methods involve contacting cells with the compound being tested for a sufficient time to allow for interaction, activation or inhibition of the TALL-1 protein or TALL-1 receptor by the compound. The period of contact with the compound being tested can be varied depending on the result being measured, and can be determined by one of skill in the art. For example, for binding assays, a shorter time of contact with the compound being tested is typically suitable, than when activation is assessed. As used herein, the term "contact period" refers to the time period during which the proteins are in contact with the compound being tested and/or the time period during which the TALL-1 protein and the TALL-1 receptor are in contact (or in a condition where contact is possible) with each other. The term "incubation period" refers to the entire time during which, for example, cells are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring. The incubation time for growth of cells can vary but is sufficient to allow for the binding of the TALL-1 receptor, activation of the receptor, and/or inhibition of the receptor. It will be recognized that shorter incubation times are preferable because compounds can be more rapidly screened. A preferred incubation time is between about 1 minute to about 48 hours.

The conditions under which the cell or cell lysate of the present invention is contacted with a putative regulatory compound and/or with other cells or cell lysates, such as by mixing, are any suitable culture or assay conditions and includes an effective medium in which the cell can be cultured or in which the cell lysate can be evaluated in the presence and absence of a putative regulatory compound. Similarly, the conditions under which soluble TALL-1 and/or TALL-1 receptors are contacted with a putative regulatory compound and/or with each other are any suitable assay conditions, such as by immobilization of the ligand or receptor on a substrate in conditions under which the ligand and/or receptor can contact the putative regulatory compound prior to, simultaneously with, or after contact of the ligand and receptor with each other.

Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. Acceptable protocols to contact a cell with a putative regulatory compound in an effective manner include the number of cells per container contacted, the concentration of putative regulatory compound(s) administered to a cell, the incubation time of the putative regulatory compound with the cell, and the concentration of compound administered to a cell. Determination of such protocols can be accomplished by those skilled in the art based on variables such as the size of the container, the volume of liquid in the container, the type of cell being tested and the chemical composition of the putative regulatory compound (i.e., size, charge etc.) being tested. A preferred amount of putative regulatory compound (s) comprises between about 1 nM to about 10 mM of putative regulatory compound(s) per well of a 96-well plate.

Suitable cells for use with the present invention include any cell that endogenously expresses a TALL-1 receptor or a TALL-1 protein as disclosed herein (such as a B lymphocyte for TALL-1 receptor or a monocyte or macrophage for TALL-1 protein), or which has been transfected with and expresses recombinant TALL-1 receptor or TALL-1 protein as disclosed herein (such as 293 cells, COS cells, CHO cells, fibroblasts, etc., genetically engineered to express TALL-1 or TALL-1 receptor). In one embodiment, host cells genetically engineered to express a functional receptor that responds to activation by TALL-1 protein can be used as an endpoint in the assay; e.g., as measured by a chemical, physiological, biological, or phenotypic change, induction of a host cell gene or a reporter gene, change in cAMP levels, adenylyl cyclase activity, host cell G protein activity, host cell kinase activity, proliferation, differentiation, etc. Cells for use with the present invention include mammalian, invertebrate, plant, insect, fungal, yeast and bacterial cells. Preferred cells include mammalian cells. Preferred mammalian cells include primate, non-human primate, mouse and rat, with human cells being preferred. Preferably, the test cell (host cell) should express a functional TALL-1 receptor that gives a significant response to interaction with a TALL-1 protein that is known to bind to and activate the TALL-1 receptor, preferably greater than 2, 5, or 10-fold induction over background.

The TALL-1 protein can be contacted with the TALL-1 receptor (or the cell expressing such receptor) prior to, simultaneous with, or after contact of the putative regulatory compound with the cell, depending on how the assay is to be evaluated, and depending on whether activation or inhibition of the receptor and/or cell expressing the receptor is to be evaluated. In one embodiment, the TALL-1 protein is contacted with the TALL-1 receptor after the cell is contacted with the putative regulatory compound so that the test compound can be evaluated for its ability to inhibit activation of the receptor by the TALL-1 protein. In another embodiment, when binding is to be evaluated, the TALL-1 protein can be contacted with the TALL-1 receptor at the same time as the test compound. Preferably, the TALL-1 protein is contacted with the cell/TALL-1 receptor in the presence and absence of the test compound for a controlled assay.

As discussed above, the step of detecting whether a putative regulatory compound binds to, activates and/or inhibits the interaction between TALL-1 and its receptor can be performed by any suitable method, including, but not limited to measurement of TALL-1 receptor transcription, measurement of TALL-1 receptor translation, measurement of phosphorylation of the TALL-1 receptor, measurement of TALL-1 receptor binding to TALL-1, measurement of TALL-1 receptor translocation within a cell, measurement of NFκB activation, measurement of TRAF5, TRAF6, NIK, IKKα and/or IKKβ activation, measurement of B cell proliferation, measurement of B cell activation, and measurement of B cell survival. Such methods of detecting an interaction of a ligand with a receptor are known in the art, and include immunoblots, phosphorylation assays, kinase assays, immunofluorescence microscopy, RNA assays, immunoprecipitation, and other biological assays.

As disclosed above, the present methods also make use of non-cell based assay systems to identify compounds that can regulate the interaction between TALL-1 and TALL-1 receptor. For example, isolated membranes may be used to identify compounds that interact with the TALL-1 receptor being tested. Membranes can be harvested from cells expressing TALL-1 receptors by standard techniques and used in an in vitro binding assay. $^{125}$I-labeled ligand (e.g., $^{125}$I-labeled TALL-1) is bound to the membranes and assayed for specific activity; specific binding is determined by comparison with binding assays performed in the presence of excess unlabeled ligand. Membranes are typically incubated with labeled ligand in the presence or absence of test compound (i.e., a putative regulatory compound). Compounds that bind to the receptor and compete with labeled ligand for binding to the membranes reduced the signal compared to the vehicle control samples.

Alternatively, soluble TALL-1 receptors may be recombinantly expressed and utilized in non-cell based assays to identify compounds that bind to TALL-1 receptors. Recombinantly expressed TALL-1 receptor polypeptides or fusion proteins containing one or more extracellular domains of TALL-1 receptor can be used in the non-cell based screening assays. Alternatively, peptides corresponding to a cytoplasmic domain of the TALL-1 receptor or fusion proteins containing a cytoplasmic domain of the TALL-1 receptor can be used in non-cell based assay systems to identify compounds that bind to the cytoplasmic portion of the TALL-1 receptor; such compounds may be useful to modulate the signal transduction pathway of the TALL-1 receptor. In non-cell based assays the recombinantly expressed TALL-1 receptor is attached to a solid substrate such as a test tube, microtiter well or a column, by means well known to those in the art. The test compounds are then assayed for their ability to bind to the TALL-1 receptor.

As discussed above, in vitro cell based assays may be designed to screen for compounds that regulate TALL-1 receptor expression at either the transcriptional or translational level. In one embodiment, DNA encoding a reporter molecule can be linked to a regulatory element of the TALL-1 receptor gene and used in appropriate intact cells, cell extracts or lysates to identify compounds that modulate TALL-1 receptor gene expression. Appropriate cells or cell extracts are prepared from any cell type that normally expresses the TALL-1 receptor gene, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound.

In any of the above-described methods of the present invention, the TALL-1 protein can be any TALL-1 protein described herein, including homologues that are capable of binding to and/or activating the receptor in the absence of

EXAMPLES

Example 1

The following example describes the identification and cloning of a nucleic acid sequence encoding TALL-1.

To identify novel members of the TNF family, the present inventors searched the GenBank EST database using the TBLASTN program for genes that were homologous to the extracellular domains of human tumor necrosis factor (TNF) and Fas ligand (FasL/ApoL). This search identified multiple EST clones that apparently encoded portions of two different human genes. These EST clones had the following GenBank Accession Nos.: AA682496, R16882, AI749928, AA166695, and T87299. The present inventors designated the first gene as Tall-1 (for TNF- and ApoL-related Leukocyte-expressed Ligand 1, see below). Sequence analysis of the above-described EST clones suggested that they were partial clones. To clone the full length Tall-1 cDNA, one of the EST clones was obtained (GenBank accession number AA682496) through the I.M.A.G.E. consortium. This EST clone was identified as a Soares fetal liver spleen INFLS S1 Homo sapiens cDNA clone. The present inventors screened a human peripheral blood leukocyte cDNA library, using the EST clones as a probe (GenBank accession number AA682496). Subsequent sequence analysis of the longest five positive clones obtained with this screening indicated that Tall-1 encodes a 285 amino acid protein, having an amino acid sequence represented herein as SEQ ID NO:2. The complete nucleic acid sequence encoding SEQ ID NO:2 is represented herein as SEQ ID NO:1. The GenBank Accession No. for the nucleic acid sequence encoding human TALL-1 is AF136293. The GenBank Accession No. for the amino acid sequence of the human TALL-1 protein is AAD29421.

With regard to the above-identified EST clones (GenBank Accession Nos.: AA682496, R16882, AI749928, AA166695, T87299), the following homology to SEQ ID NO:1 was noted, using BLAST 2 alignment with the 0BLOSUM62 matrix as described elsewhere herein. The nucleic acid sequence of EST clone AA682496 (positions 80 to 456), a human Soares fetal liver spleen INFLS_S1 cDNA clone, is 100% identical to the reverse complement of nucleotide positions 482 to 858 (377 nucleotides) of SEQ ID NO:1. The nucleic acid sequence of EST clone R16882 (positions 89 to 360), a human Soares fetal liver spleen cDNA clone, is 94% identical to the reverse complement of nucleotide positions 592 to 858 (267 nucleotides) of SEQ ID NO:1. The nucleic acid sequence of EST clone AI749928 (positions 75 to 437), a human Barstead aorta cDNA clone, was 100% identical to the reverse complement of nucleotide positions 496 to 858 (363 nucleotides) of SEQ ID NO:1. The nucleic acid sequence of EST clone AA166695 (positions 81 to 446), a Stratagene ovarian cancer human cDNA clone, was 98% identical to the reverse complement of nucleotide positions 489 to 858 (370 nucleotides) of SEQ ID NO:1. The nucleic acid sequence of EST clone T87299 (positions 96 to 363), a Soares fetal liver spleen human cDNA clone, was 94% identical to the reverse complement of nucleotide positions 596 to 858 (263 nucleotides) of SEQ ID NO:1.

Structural analysis of the SEQ ID NO:2 suggests that TALL-1 is a type II transmembrane protein. The C-terminal part of the extracellular domain of TALL-1 shares approximately 20–25% sequence identity with the corresponding domains of TNF (FIG. 1B, SEQ ID NO:4), FasL (FIG. 1B, SEQ ID NO:5), Lymphotoxin-α (FIG. 1B, SEQ ID NO:6), and TRAIL (FIG. 1B, SEQ ID NO:7). Referring to FIG. 1B, the conserved β-strands are underlined, and homologous regions are boxed with identical residues shaded. FIG. 1B to shows that the sequence homology is primarily limited to the residues forming several β-strands. These data suggest that TALL-1 is a member of the TNF family, and like some other members of the TNF family, folds into an anti-parallel β-sandwich structure (Banner et al., (1993), Cell 73:431–445; Eck et al., (1989), J. Biol. Chem. 267:2119–2122).

Sequence analysis of the EST clones encoding the second TNF/FasL like gene, which us the present inventors designated as TALL-2, indicated that this gene is identical to the recently described molecule APRIL (Hahne et al., (1998), J. Exp. Med. 188:1185–1190). The GenBank Accession No. for the nucleic acid sequence encoding TALL-2 is AF136294. The GenBank Accession No. for the TALL-2 protein is AAD29422. The C-terminal region of the extracellular domain of TALL-2/APRIL (FIG. 1B, SEQ ID NO:3) also shares about 20–25% sequence identity with those of TNF, FasL, TRAIL and Lymphotoxin-α. Interestingly, as shown in FIG. 1A, the C-terminal regions of the extracellular domains of TALL-1 (SEQ ID NO:2) and TALL-2/APRIL (SEQ ID NO:3) share ~35% sequence identity with each other, significantly higher than with other members of the TNF family. Referring to FIG. 1A, the putative transmembrane domains of TALL-1 and TALL-2/APRIL are underlined, and homologous regions are boxed with identical residues shaded. In addition to the C-terminal regions of the extracellular domains, the homology between TALL-1 and TALL-2/APRIL extends to other parts of the molecules, including the N-terminal region of the extracellular domains, the transmembrane and the intracellular domains (FIG. 1A). This data suggests that TALL-1 and TALL-2/APRIL belong to a subfamily of the TNF family of ligands.

Northern blot analysis suggested that human TALL-1 is expressed abundantly in peripheral blood leukocytes (PBLs) and weakly in spleen as a single 2.4 kb transcript (FIG. 2A). Briefly, multiple human tissue blots were purchased from Clontech and were hybridized under high stringency conditions according to the manufacturer. Specifically, the blots were hybridized with Clontech's Rapid Hybridization Buffer at 68° C. for 2 hours. The blots were washed in 2×SSC/0.1% SDS at room temperature for 10 minutes, followed by 0.1×SSC/0.1% SDS at 68° C. for 30 minutes. The molecular size standards (in kilobases) are shown in FIG. 2A on the left. FIG. 2A shows that TALL-1 is barely detectable in all other tissues examined (FIG. 2A). Interestingly, Northern blot analysis indicated that the highest level of APRIL is also detected in peripheral blood leukocytes (data not shown, Tan et al., (1997), Gene 204:35–46).

Figure 2B:
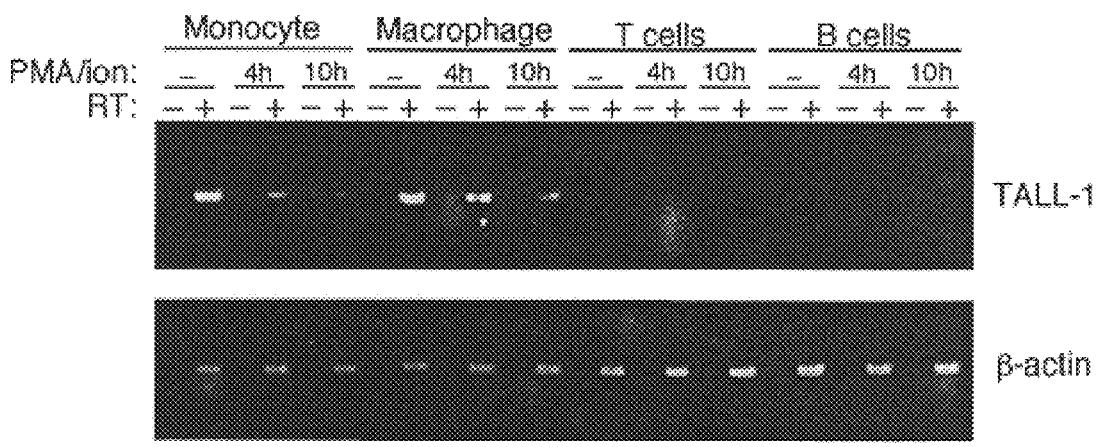
FIG. 2B is a digitized image of an RT-βCR analysis showing Tall-1 mRNA expression in isolated primary leukocytes.

To identify the specific cell types in PBLs that express TALL-1, the present inventors performed reverse transcriptase-polymerase chain reaction (RT-PCR) analysis with RNAs extracted from isolated human peripheral monocytes, macrophages, T and B lymphocytes. Briefly, human peripheral blood monocytes and macrophages were isolated as described (Nedwin et al., (1985), J. Immunol. 135:2492–2498). Human peripheral T lymphocytes were isolated from monocyte/macrophage depleted lymphocytes using anti-CD2 magnetic beads (Dynal, Inc.) by following procedures suggested by the manufacture. B cells were isolated by T cell deletion of the lymphocytes. The isolated cells were treated with PMA (10 ng/ml)/ionomycin (500 ng/ml) for 4 or 10 hours, or left untreated. Total RNAs were then extracted and RT-PCR experiments were performed with the primers corresponding to the sequences of TALL-1 or β-actin cDNAs, using a standard protocol as described in Sambrook et al. This experiment demonstrated that TALL-1 was constitutively expressed in untreated monocytes and macrophages, but not in peripheral T and B lymphocytes (FIG. 2B). The mRNA level of TALL-1 was down-regulated by PMA/ionomycin treatment in both monocytes and macrophages (FIG. 2B). Similarly, it was determined that TALL-2/APRIL was also specifically expressed in monocytes and macrophages, and its expression was downregulated by PMA/ionomycin treatment (data not shown).

Figure 3:
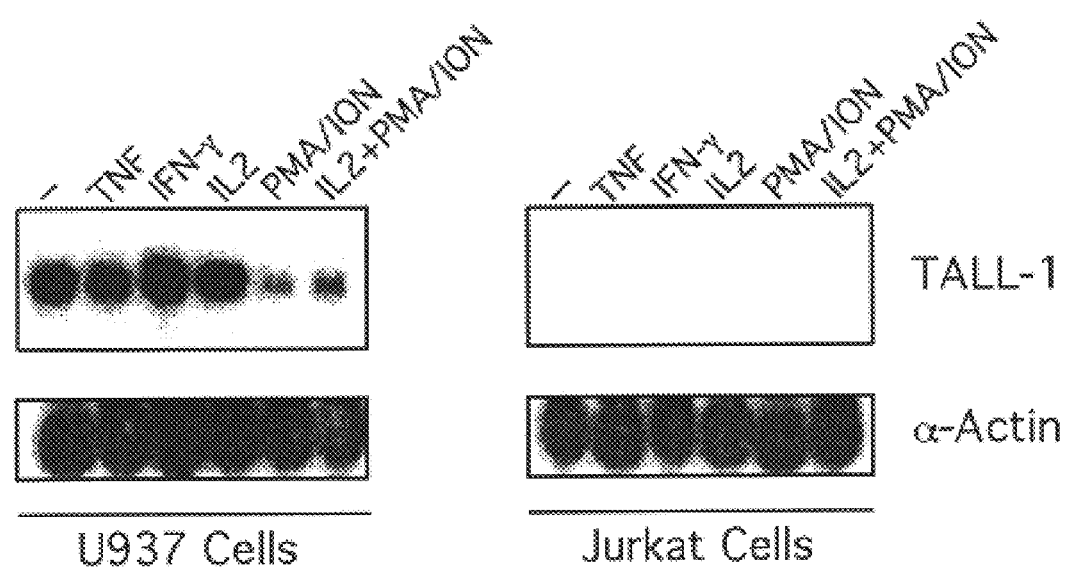
FIG. 3 is a digitized image of a Northern blot analysis showing Tall-1 gene expression in U937 and Jurkat cells treated with various stimulatory agents.

Consistent with these observations, Northern blot analysis showed that TALL-1 was abundantly and constitutively expressed in the monocytic cell line U937, but not in the T cell line Jurkat (FIG. 3). Briefly, U937 and Jurkat cells were treated with recombinant human tumor necrosis factor (TNF; 20 ng/ml), interferon-γ (IFN-γ; 20 ng/ml), interleukin-2 (IL-2; 20 units/ml), phorbol myristate acetate (PMA; 10 ng/ml)/ionomycin (500 ng/ml), or IL-2 plus PMA/ionomycin for 10 hours, or left untreated. Cells were then harvested and total RNAs were isolated for Northern blot analysis with human Tall-1 cDNA probe. The same blots were stripped and reprobed with human α-actin probe. In U937 cells, TALL-1 expression was also dramatically down-regulated by PMA/ionomycin, while TNF, IFN-γ, and IL-2 had no effect on TALL-1 expression (FIG. 3). These data are surprising in that many TNF family members, such as TNF, FasL, Lymphotoxin-α, and LIGHT, are mostly expressed in activated, but minimally or not at all in unstimulated immune cells, and are up-regulated by mitogens (Mauri et al., (1998), *Immunity* 8:21–30; Svedersky et al., *J. Immunol.* 134:1604–1608; Nedwin et al., (1985), *J. Immunol.* 135:2492–2498).

Figure 4:
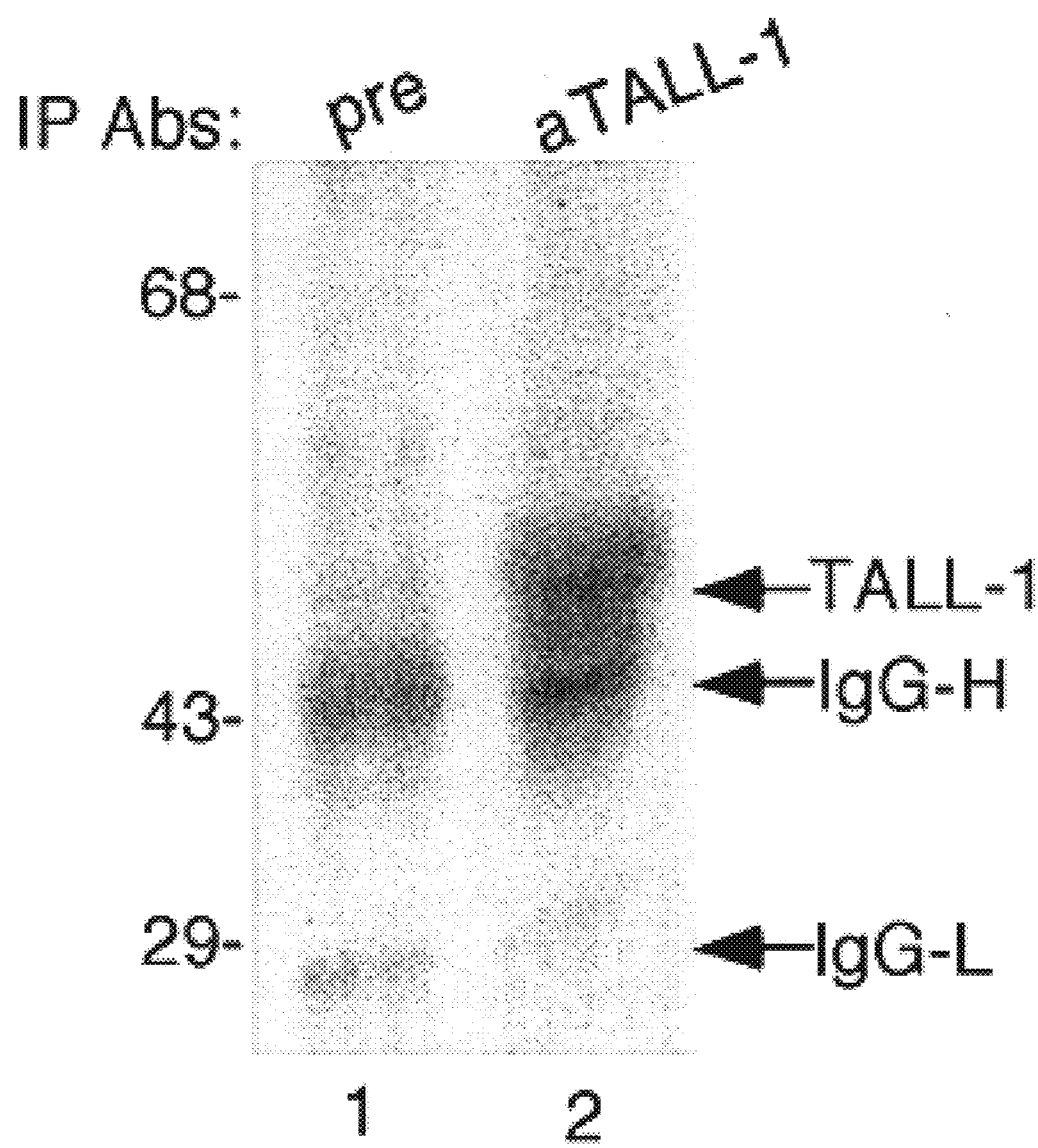
FIG. 4 is a digitized image of a western blot showing detection of TALL-1 protein in U937 cells.

To determine whether TALL-1 gene encodes an expressed protein, a peptide-directed rabbit polyclonal antibody was raised against a fragment of the extracellular domain of TALL-1. Immunoprecipitation and western blot experiments with this antibody indicated that TALL-1 is expressed as a ~52 kDa protein in U937 cells (FIG. 4). Briefly, lysates of U937 cells (1×10⁷) were immunoprecipitated with 1 ml preimmune serum control or a rabbit polyclonal antibody against human TALL-1. The immunoprecipitates were analyzed by western blot with the TALL-1 antibody. The molecular size standards (kDa) are shown to the left in FIG. 4 (IgG-H=IgG heavy chain; Ig-L=IgG light chain; pre= preimmune serum; αTALL-1 =anti-TALL-1 antibody). The molecular weight of the TALL-1 protein detected was larger than that which was deduced from the amino acid sequence. This may be due to its post-translational modification by glycosidation, which is true for most, if not all members of the TNF family.

TALL-1 and TALL-2/APRIL, either alone or together, do not induce apoptosis or NF-κB and AP1 activation in several cell lines, including 293, Jurkat, and U937 (data not shown). The intracellular signaling pathways and the biological effects triggered by TALL-1 are described in more detail in the examples below. TALL-1 and its receptor, TALL-1 receptor, are clearly involved in monocyte/macrophage and B-lymphocyte-mediated immunological processes. Modify according to what is now known.

Example 2

The following example demonstrates that TALL-1 co-immunoprecipitates with B Cell Maturation Protein (BCMA)

To identify the receptor for TALL-1, the present inventors employed a candidate approach. Since all identified TNF family members bind to receptors belonging to the TNF receptor family, the present inventors speculated that the receptor for TALL-1 would also be a member of the TNF receptor family whose expression is limited to B lymphocytes. Previously, a TNF receptor family member, B Cell Maturation Protein (BCMA), was identified during the analysis of a t(4;1)(q26;13) chromosomal translocation occurred in a human malignant T cell lymphoma (Laabi et al., (1992), *EMBO J.* 11:3897–3904). The breakpoints of the two chromosome partners involve the IL-2 gene on chromosome 4 and the BCMA gene on chromosome 16. The translocation results in the transcription of a hybrid IL-2-BCMA mRNA composed of the first three exons of IL-2 at the 5' end fused to the coding sequences of BCMA mRNA at the 3 end (Laabi et al., (1992), *EMBO J.* 11:3897–3904). RNA protection analysis indicates that BCMA mRNA is expressed in most B lymphocyte-derived but not in non-B lymphocyte-derived cell lines (Laabi et al., (1994), *Nucleic Acids Research* 22:1147–1154; Gras et al., (1995), *International Immunology* 7:1093–1106). In human tissues, BCMA is expressed by spleen and lymph nodes, but not by brain, muscle, heart, lung, kidney, pancreas, testis, and placenta. Using human malignant B cell lines characteristic of different stages of B lymphocyte differentiation, it has been shown that BCMA mRNA is absent in the pro-B lymphocyte stage and its expression increases with B lymphocyte maturation (Laabi et al., (1994), *Nucleic Acids Research* 22:1147–1154; Gras et al., (1995), *International Immunology* 7:1093–1106). The physiological functions of BCMA, however, had not been determined prior to the present invention, and no one had suggested or identified a ligand for the receptor. The present inventors sought to determine whether BCMA was the receptor for TALL-1.

Initially, a soluble TALL-1 (sTALL-1) was produced in a human embryonic kidney 293 cell line. Prior to this experiment, it had been shown that the transmembrane TALL-1 precursor is cleaved between amino acid residues R133 and A134 to form sTALL-1 (Schneider et al., (1999), *J. Exp. Med.* 189:1747–1756). To produce sTALL-1, the present inventors constructed a mammalian secretion expression construct in which an N-terminal Flag epitope was fused in frame with a cDNA fragment encoding positions 134–285 of the amino acid sequence of TALL-1 (positions 134-285 of SEQ ID NO:2). Specifically, the cDNA fragment was amplified from a TALL-1 full-length cDNA clone[6] by PCR with the following two primers: 5'-GGAAGCTTATGGACTACAAGGACGACGATG-3' (SEQ ID NO:8) and 5'-AAAGGATCCTACAGACATGGTGTAAGTAG-3' (SEQ ID NO:9). The PCR product was digested with Hind III and BamHI, and inserted into the Hind III and BamHI sites of the pSec-Tag2B plasmid (Invitrogen, Carlsbad, Calif.) to make pSec-Flag-sTALL-1. This construct was transiently or stably transfected into 293 cells.

Figure 5A:
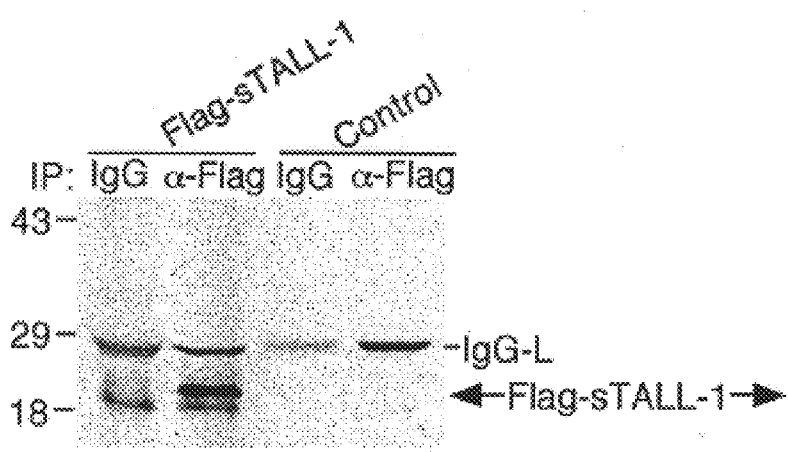
FIG. 5A is a digitized image of a western blot showing expression of Flag-sTALL-1.

To detect Flag-sTALL-1 expression,293 cells (3×10⁶/100 dish) were transfected with 10 µg of pSec-Flag-sTALL-1 or the empty control pSec-TaqB2 plasmid by $Ca^3(PO^4)_2$ precipitation (Hu et al., (1999), *J. Biol. Chem.* 274:30603–30610; Shu et al., (1997), *Immunity* 6:751–763). 24 hours after transfection, cell culture medium was collected. A 1 ml aliquot of the medium was incubated with 0.5 μg anti-Flag monoclonal antibody (Sigma, St. Luis, Mo.) (FIG. 5A; lanes 2 & 4) or 0.5 μg control mouse IgG (FIG. 5A; lanes 1 & 3), and 25 μl of a 1:1 slurry of GammaBind G Plus Sepharose (Pharmacia, Uppsala, Sweden) at 4° C. for 3 hours. The sepharose beads were washed three times with 1 ml lysis buffer. The precipitates were fractionated on SDS-PAGE and western blot analysis was performed with the anti-Flag antibody (Sigma). Western blots were performed as described (Hu et al., 1999; Shu et al., 1997). FIG. 5A confirms that Flag-tagged sTALL-1 (Flag-sTALL-1) was expressed in the culture medium.

Figure 5B:
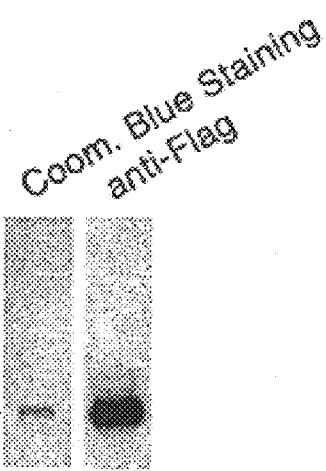
FIG. 5B is a digitized image of a western blot indicating purification of Flag-sTALL-1.

The secreted Flag-sTALL-1 was also purified with an anti-Flag antibody affinity column (FIG. 5B). To purify Flag-sTALL-1, 500 ml of conditioned medium from the 293 stable cell line expressing Flag-sTALL-1 was collected and supplemented with 10 mM Tris (pH7.5) and 100 mM NaCl. 2 ml of anti-Flag antibody affinity chromatography column (Sigma, St. Luis, Mo.) was pre-washed with three sequential 5 ml of aliquots of 0.1 M glycine (pH3.5) and followed by three sequential 5 ml of TBS buffer (50 mM Tris, 150 mM NaCl, pH7.4). The medium was passed through the column and the column was washed with 12 ml aliquots of TBS for three times. The proteins bound to the column were eluted with 100 μg/ml Flag peptide (Sigma, St. Luis, Mo.) and analyzed by Coomassie blue staining (FIG. 5B; left lane) or Western blot with anti-Flag antibody (FIG. 5B; right lane).

To determine whether TALL-1 binds to BCMA, the present inventors next constructed a mammalian expression construct for C-terminal HA epitope-tagged BCMA (BCMA-HA). To construct the mammalian expression plasmid for C-terminal HA-tagged BCMA, a cDNA fragment encoding BCMA (SEQ ID NO:10) and a C-terminal HA epitope was amplified by PCR from an EST clone (GenBank Accession No. AA259026) with the following two primers:

5'-ATAAGCTTTTTGTGATGATGTTG-3' (SEQ ID NO:12); and,

5'-TTGGATCCTTAAGCGTAATCTGGAACATCGTAT GGGTACCTAGCAGAAATTGAT-3' (SEQ ID NO:13).

The amplified cDNA fragment was digested with Hind III and BamH I and cloned into the Hind III and BamH I site of a CMV promoter based plasmid to make pCMV-BCMA-HA.

Figure 6A:
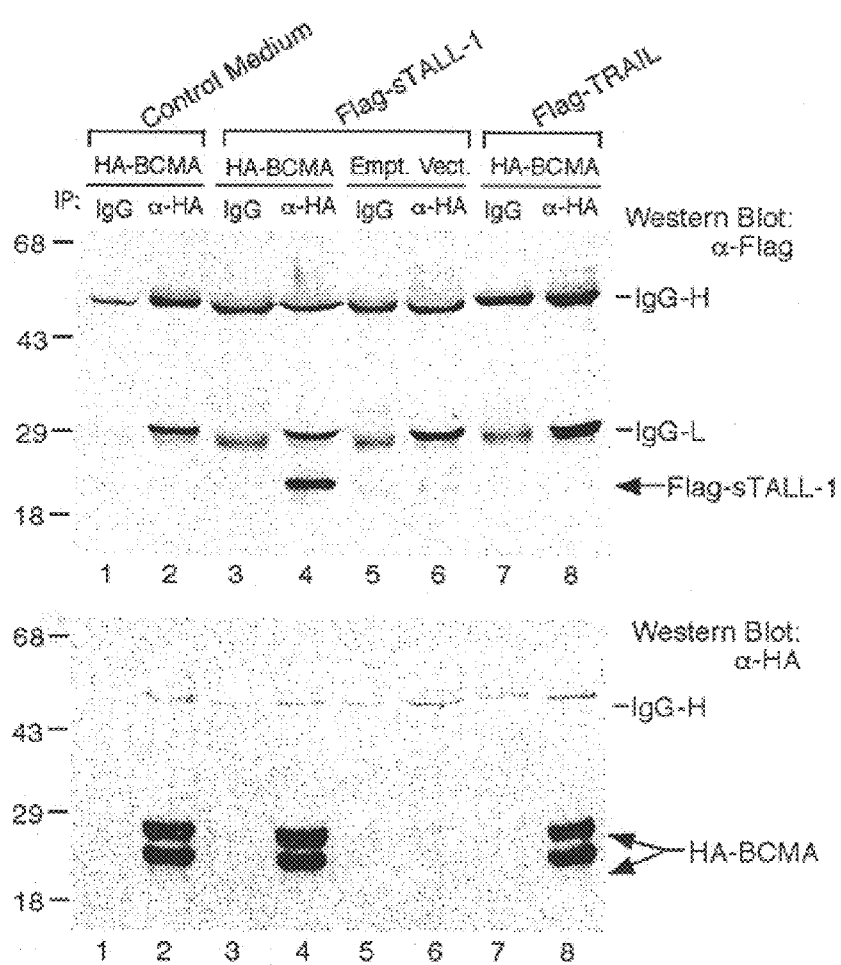
FIG. 6A is a digitized image of a western blot showing that BCMA interacts with sTALL-1 but not with sTRAIL.

To detect interaction between Flag-sTALL-1 and BCMA-HA, 293 cells (3×10$^6$/100 mm dish) were transfected with 10 μg of the expression plasmid for BCMA-HA (FIG. 6A; lanes 1–4,7,8) or an empty control plasmid (FIG. 6A; lanes 5 & 6). 24 hours after transfection, cells were lysed in 1.0 ml lysis buffer (20 mM Tris [pH 7.5], 150 mM NaCl, 1% Triton, 1 mM EDTA, 10 μg/ml aprotinin, 10 μg/ml leupeptin, 1 mM PMSF). The lysates were mixed with 5 ml of control conditioned medium (FIG. 6A; lanes 1&2; cell culture medium from the empty pSec-TagB2 plasmid transfected 293 cells), Flag-sTALL-1 containing medium (FIG. 6A; lanes 3–6), or control conditioned medium plus 0.1 μg recombinant Flag-sTRAIL (provided by Dr. Bryant Barnay) (FIG. 6A; lanes 7 & 8). The mixtures were split into 2 aliquots and each aliquot was incubated with 0.5 μg anti-HA monoclonal antibody (BABCO, Berkeley, Calif.) (FIG. 6A; lanes 2,4,6,8) or control mouse IgG (FIG. 6A; lanes 1, 3, 5, 7), and 25 μl of a 1:1 slurry of GammaBind G Plus Sepharose at 4° C. for 3 hours. The sepharose beads were washed three times with 1 ml lysis buffer containing 500 mM NaCl. The precipitates were analyzed by Western blot with anti-Flag antibody (FIG. 6A; upper panel). The same blot was stripped and reprobed with anti-HA antibody (FIG. 6A; lower panel). All conditioned medium was supplemented with 10 mM Tris (pH7.5), 100 mM NaCl, 1 mM EDTA, 10 μg/ml aprotinin, 10 μg/ml leupeptin, and 1 mM PMSF before TH immunoprecipitation experiments. Western blots were performed as described above. As shown in FIG. 6A, co-immunoprecipitation and Western blot analysis indicated that BCMA-HA interacted with Flag-sTALL-1. BCMA-HA did not interact with proteins in control medium or Flag-tagged soluble TRAIL (Flag-sTRAIL) (FIG. 6A), another member of the TNF family (Nataga, (1997), *Cell* 88:355–365; Ashkenazi et al., (1999), *Curr. Opin. Cell Biol.* 11:255–260). The higher molecular weight band in FIG. 6A is probably a glycosylated form of BCMA, which has been shown to be a glycoprotein (Gras et al., (1995), *International Immunology* 7:1093–1106).

To determine whether the binding of TALL-1 to BCMA is specific or whether TALL-1 non-specifically binds to any member of the TNF receptor family, the present inventors next examined whether Flag-sTALL-1 interacts with TRAIL-R1/DR4 and TRAIL-R2/DR5, two receptors for TRAIL (Pan et al., (1997), *Science* 276:111–113; Pan et al., (1997), *Science* 277:815–817). To do this, conditioned medium containing Flag-sTRAIL-R1-Fc (Pan et al., (1997), *Science* 276:111–113) or Flag-sTRAIL-R2-Fc (Pan et al., (1997), *Science* 277:815–817) fusion protein was mixed with conditioned medium containing Flag-sTALL-1 or Flag-sTRAIL. The expression plasmids for Flag-sTRAIL-R1-Fc and Flag-sTRAIL-R2-Fc were provided by Dr. Claudio Vincenz. The production of these constructs is described in Pan et al., 1997, "The receptor for the cytotoxic ligand TRAIL", *Science* 276:111–113; and in Pan et al., 1997, "An antagonist decoy receptor and a death domain-containing receptor for TRAIL", *Science* 277:815–817; both of which are incorporated herein by reference in their entireties.

Figure 6B:
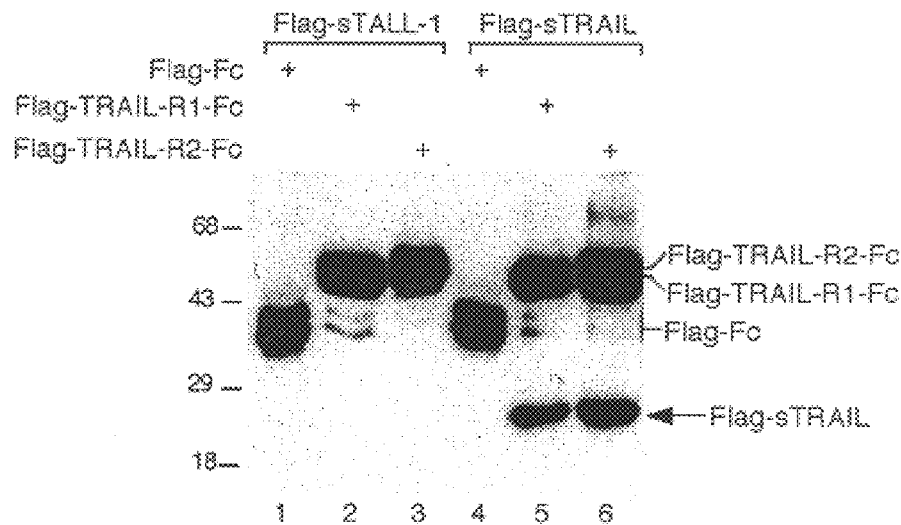
FIG. 6B is a digitized image of a western blot showing that sTALL-1 does not bind to TRAIL receptors.

To detect the interaction between Flag-sTALL-1 or Flag-sTRAIL and Flag-TRAIL-R1-Fc or Flag-TRAIL-R2-Fc, 293 cells (3×10$^6$/100 dish) were transfected with 10 μg of the mammalian secretion expression plasmid for Flag-sTRAIL-R1-Fc, Flag-sTRAIL-R2-Fc, or Flag-Fc control. Cell culture medium was collected 24 hours after transfection. 3 ml aliquot of the medium was mixed with 3 ml of Flag-sTALL-1 (FIG. 6B; lanes 1–3) or Flag-sTRAIL (FIG. 6B; lanes 4–6) containing medium. The mixture was incubated with 25 μl of a 1:1 slurry of GammaBind G Plus Sepharose at 4° C. for 3 hours. The beads were washed with the lysis buffer three times. The precipitates were analyzed by Western blot with anti-Flag antibody as described above. As above, all conditioned medium was supplemented with 10 mM Tris (pH7.5), 100 mM NaCl, 1 mM EDTA, 10 μg/ml aprotinin, 10 μg/ml leupeptin, and 1 mM PMSF before TH immunoprecipitation experiments. As shown in FIG. 6B, Flag-sTALL-1 does not interact with TRAIL-R1 and TRAIL-R2. As expected, Flag-sTRAIL interacted with TRAIL-R1 and TRAIL-R2 in the same experiment (FIG. 6B). Taken together, these experiments suggest that TALL-1 specifically (i.e., selectively) interacts with BCMA.

Example 3

The following example demonstrates that BCMA can be targeted to the plasma membrane where it can bind to sTALL-1.

Although it has been experimentally demonstrated that BCMA can insert into canine microsomes as a glycosylated type I integral membrane protein in vitro (Gras et al., (1995), *International Immunology* 7:1093–1106), immunocytochemistry and subfractionation studies indicated that BCMA was enriched in Golgi apparatus and failed to detect BCMA on the plasma membrane (Gras et al., 1995, ibid.). In addition, sequence analysis suggests that BCMA has no recognizable signal peptide at its N-terminus (Laabi et al., (1992), *EMBO J.* 11:3897–3904; Laabi et al., (1994), *Nucleic Acids Research* 22:1147–1154; Gras et al., (1995), *International Immunology* 7:1093–1106). These observations raise the question of whether BCMA can function as a plasma membrane-bound receptor. To resolve this question, the present inventors performed flow cytometry analysis. To do this, we first tested whether the Flag-sTALL-1 protein produced by the present inventors could bind to its receptor on the plasma membrane of the B lymphocyte-derived Bjab cell line, which has been shown to express the previously unidentified TALL-1 receptor (Schneider et al., 1999). For most flow cytometry experiments described in this example, cells (1×10⁶) were incubated with 500 µl control medium (from the empty control pSec-TagB2 plasmid transfected 293 cells) (FIG. 7A; shaded histograms) or with Flag-sTALL-1 containing medium (FIG. 7A; solid line histograms) for 40 minutes. Cell staining was performed by sequential incubation (each 40 minutes) with anti-Flag monoclonal antibody (1 µg/ml) and RPE-conjugated goat anti-mouse IgG (1:200 dilution) in staining buffer (D-βBS containing 2% fetal bovine serum). Cells were washed two times with staining buffer following each incubation. The fluorescence exhibited by the stained cells was measured using a Becton Dickenson FACScan flow cytometer.

Figure 7A:
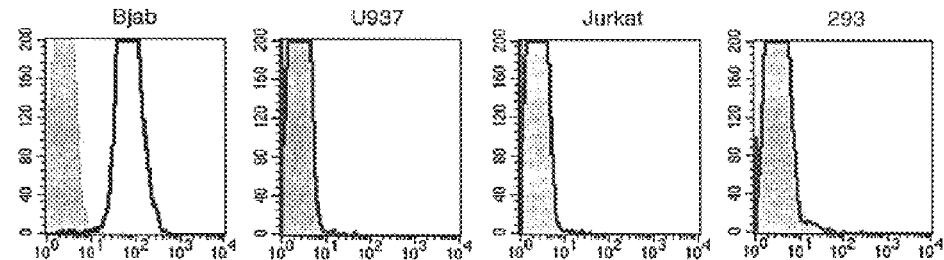
FIG. 7A is a flow cytometry histogram showing TALL-1 receptor expression in various cell lines detected by Flag-sTALL-1.

As shown in FIG. 7A, flow cytometry analysis indicates that Flag-sTALL-1 can bind to the plasma membrane of Bjab cells, but not of the monocytic U937 cells, the T lymphoma Jurkat cells, or the embryonic kidney 293 cells. These data suggest that Bjab, but not U937, Jurkat or 293 cells, express the TALL-1 receptor.

To test whether BCMA can function as a membrane receptor, 293 cells were transfected with the expression plasmid for BCMA, described in Example 2 above. As controls, 293 cells were also transfected with empty control plasmid (described above), with CD40 (provided by Dr. David Goeddel) or with TNF-R2 (provided by Dr. David Goeddel). 24 hours after transfection, cells were incubated with control medium (shaded histogram) or Flag-sTALL-1 containing medium (solid line histogram), and flow cytometry analysis of the transfected intact cells was performed with anti-Flag antibody as described above.

Figure 7B:
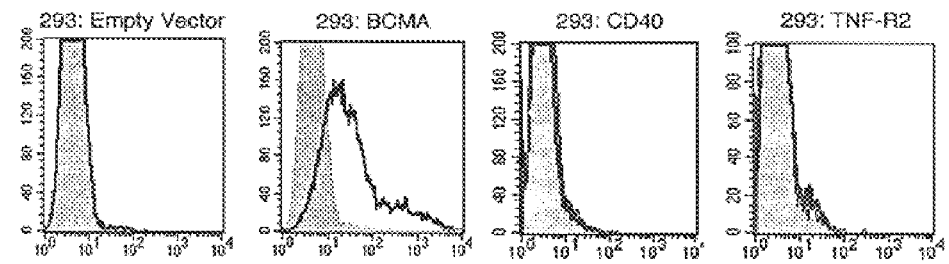
FIG. 7B is a flow cytometry histogram showing that BCMA is targeted to plasma membrane where it can bind to sTALL-1.

As shown in FIG. 7B, Flag-sTALL-1 could bind to the plasma membrane of BCMA transfected cells, but not to cells transfected with the empty control plasmid, with CD40 or with TNF-R2 transfected cells. These data indicate that BCMA can be targeted to the plasma membrane, and that sTALL-1 specifically binds to the plasma membrane-bound BCMA but not to other examined TNF receptor family members. It is noted that some well established TNF receptor family members, such as human TNF-R1, TRAIL-R4 (Degli-Esposti et al., (1997), *Immunity* 7:813–820), and HVEM (Montgomery et al., (1996), *Cell* 87:427–436) also do not have a recognizable signal peptide based on structural analysis with existing software programs (data not shown). In addition, many examined TNF receptor family members, such as TNF-R1 and Fas, are found to be enriched in the Golgi apparatus and not or barely detectable on plasma membrane by immunocytochemistry and subfractionation experiments (Bennett et al., (1998), *Science* 282:290–293; Jones et al., (1999), *J. Immunol.* 162:1042–1048; Cottin et al., (1999), *J. Biol. Chem.* 274:32975–32987). However, flow cytometry analysis, a more sensitive method, could easily detect TNF-R1 and Fas on plasma membrane in the same cell types (Bennett et al., (1998), *Science* 282:290–293; Jones et al., (1999), *J. Immunol.* 162:1042–1048). This is the first demonstration that BCMA shares this feature with other TNF receptor family members.

Example 4

The following example demonstrates that soluble BCMA inhibits TALL-1 binding to Bjab cells and inhibits TALL-1-triggered B lymphocyte proliferation.

To determine whether TALL-1 signals through BCMA, the present inventors next investigated whether soluble BCMA (sBCMA) could block the binding of TALL-1 to its receptor on Bjab cells and whether sBCMA could inhibit TALL-1-triggered B lymphocyte proliferation. To determine whether soluble BCMA (sBCMA) could block the binding of TALL-1 to its receptor, a secreted fusion protein Flag-sBCMA-Fc, which consisted of an N-terminal Flag tag, the extracellular domain of BCMA (amino acid positions 1–62 of SEQ ID NO:11) and the Fc fragment of immunoglobulin G1 (IgG1) was produced. Specifically, to construct a mammalian secretion expression plasmid for soluble BCMA and Fc fusion protein, a cDNA encoding amino acid positions 1–62 of human BCMA (SEQ ID NO:11) was amplified by PCR from the EST clone AA259026 (described above) with the following two primers: 5'-GGGAATTCCATGTTGCAGATGGCTG-3' (SEQ ID NO:14) and 5'-GGGGATCCAAACAGGTCCAGAG-3' (SEQ ID NO:15). The PCR product was digested with EcoR I and BamH I and inserted into the EcoR I and Bgl II sites of the pCMV1-Flag-Fc plasmid (Pan et al., (1997), *Science* 276:111–113) to make pCMV1-Flag-sBCMA-Fc. To produce soluble BCMA for use in the experiment, 293 cells (3×10⁶/100 mm dish) were transfected with 10 µg of pCMV1-Flag-sBCMA-Fc plasmid. 12 hours later, cells were washed with PBS and fresh medium was added. 36 hours after that, cell culture medium was collected and concentrated for 50 folds by centrifugation with Centricon-30 (Millipore, Bedford, Mass.).

Figure 7C:
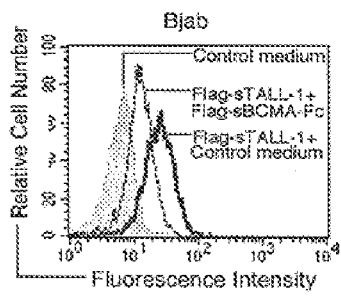
FIG. 7C is a flow cytometry histogram showing that sBCMA blocks the binding of sTALL-1 to its receptor.

Bjab cells were incubated with 500 µl control medium (FIG. 7C, shaded histogram), 250 µl Flag-sTALL-1 containing medium plus 250 µl control medium (FIG. 7C, solid line histogram), or 250 µl Flag-sTALL-1 medium plus 250 µl concentrated Flag-sBCMA-Fc containing medium (FIG. 7C, dashed line histogram). As described in Examples 2 and 3, cell staining was performed by sequential incubation (each 40 minutes) with anti-Flag monoclonal antibody (1 µg/ml) and RPE-conjugated goat anti-mouse IgG (1:200 dilution) in staining buffer (D-PBS containing 2% fetal bovine serum). Cells were washed two times with staining buffer following each incubation. The fluorescence exhibited by the stained cells was measured using a Becton Dickson FACScan flow cytometer. As shown in FIG. 7C, this experiment demonstrated that Flag-sBCMA-Fc partially blocked sTALL-1 binding to its receptor on Bjab cells.

Figure 8:
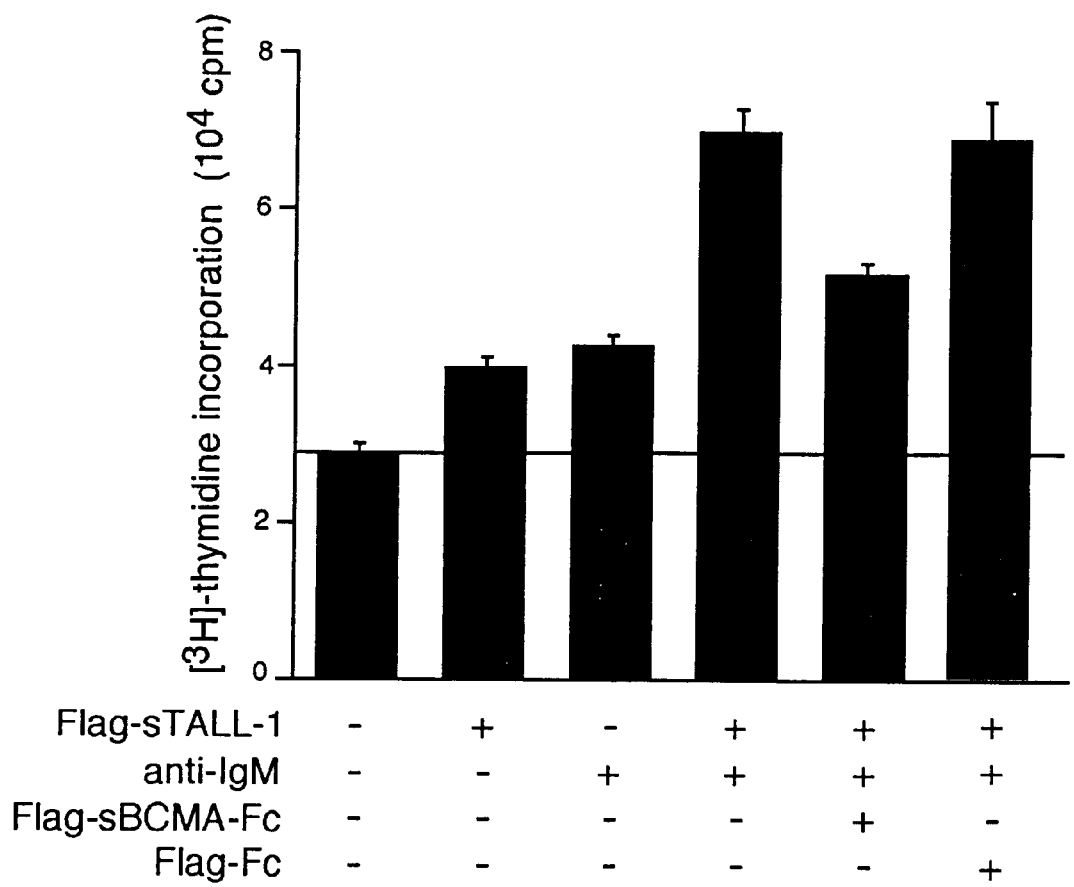
FIG. 8 is a bar graph demonstrating inhibition of TALL-1 triggered B cell co-stimulation by sBCMA.

To determine whether sBCMA could inhibit TALL-1-triggered B lymphocyte proliferation, human peripheral B lymphocytes were purified from peripheral blood of health donors using anti-CD19 dynal beads and DETACHaBEADanti-CD19 (Dynal Inc., Lake Success, N.Y.) following procedures suggested by the manufacture. Purified B lymphocytes (1×10⁵) were seeded on 96-well dishes and treated with the following reagents for 40 hours: 1. TBS control buffer; 2. Flag-sTALL-1 (100 ng/ml); 3. Anti-IgM (10 µg/ml); 4. Flag-sTALL-1 (100 ng/ml)+anti-IgM (10 µg/ml); 5. Flag-sTALL-1 (100 ng/ml)+anti-IgM (10 µg/ml)+concentrated Flag-sBCMA-Fc (5 µl); 6. Flag-sTALL-1 (100 ng/ml)+anti-IgM (10 µg/ml)+concentrated Flag-Fc (5 µl). Cells were then pulsed for an additional 10 hours with [³H]-thymidine (1 μCi/well) (NEN Life Biotechnology, Boston, Mass.). Incorporation of [³H]-thymidine was measured by liquid scintillation counting. The data shown in FIG. 8 are averages and standard deviations of one representative experiment in which each treatment had been performed in triplicate. FIG. 8 demonstrates that Flag-sBCMA-Fc, but not Flag-Fc, significantly (p<0.01) inhibited sTALL-1-triggered B lymphocyte proliferation. These data are consistent with the conclusion that TALL-1 signals through BCMA.

Example 5

The following example demonstrates that BCMA activates NF-κB and this activation is potentiated by sTALL-1.

Many members of the TNF receptor family can activate NF-κB when overexpressed in mammalian cells (Baker and Reddy, 1998; Rothe et al., 1995; Hu et al., 1999). To determine whether BCMA can also activate NF-κB, 293 cells were transfected with a mammalian expression plasmid for BCMA as described above (i.e., the BCMA-HA plasmid). Briefly, 293 cells were transfected with 0.5 μg of NF-κB luciferase reporter plasmid and increased amounts of an expression plasmid for BCMA. 14 hours after transfection, cells were treated with 100 ng/ml Flag-sTALL-1 (FIG. 9, black bars) or were left untreated (FIG. 9, white bars) for 7 hours and luciferase reporter assays were performed. The luciferase reporter gene assays were performed as described (Smith et al., (1994), Cell 76:959–963; Wong et al., (1997), J. Biol. Chem. 272:25190–25195). Within the same experiment, each transfection was performed in triplicate, and where necessary, enough of the empty control plasmid was added so that each transfection received the same amount of total DNA. To normalize for transfection efficiency and protein amount, 0.5 μg of RSV-β-gal plasmid was added to all transfections. Luciferase activities were normalized on the basis of β-galactosidase expression levels. Data shown in FIG. 9 are averages and standard deviations of one representative experiment in which each transfection had been performed in triplicate.

Figure 9:
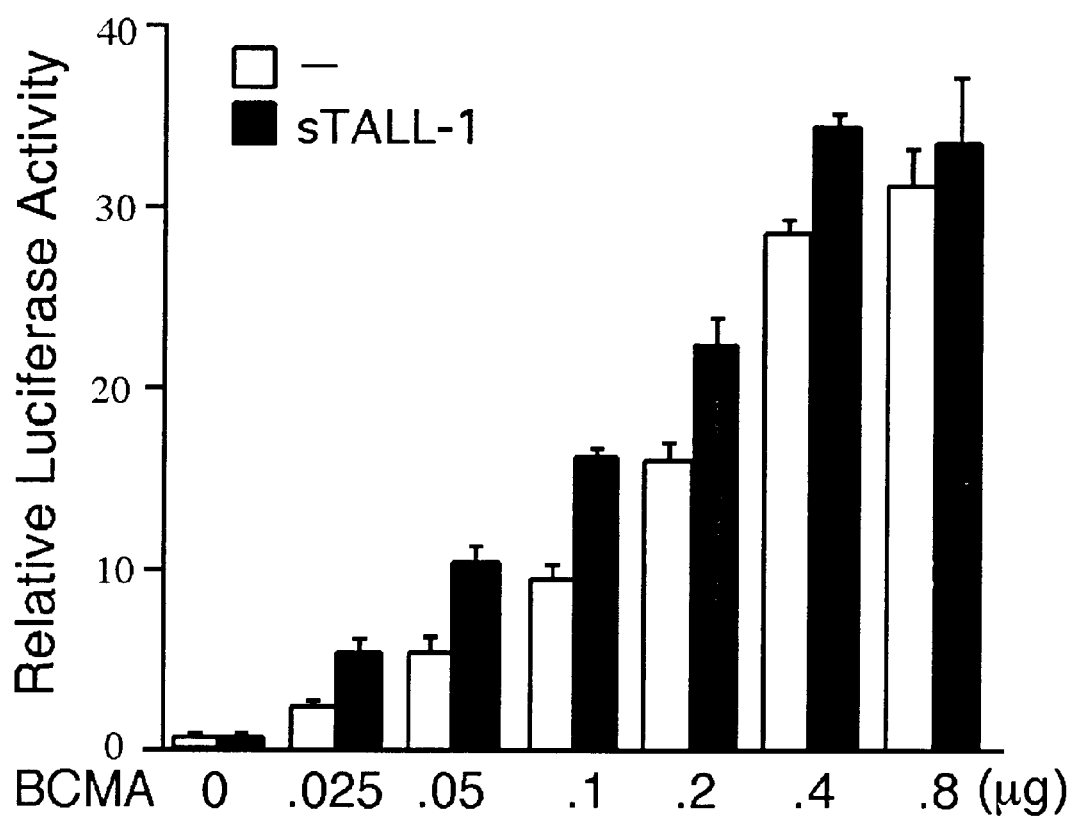
FIG. 9 is a bar graph showing that BCMA activates NF-κB and that the activation is potentiated by sTALL-1.

The luciferase reporter gene assays indicated that transfection of BCMA activated NF-κB in a dose dependent manner in 293 cells (FIG. 9). Transfection of BCMA did not activate an interferon response factor in reporter gene assays (data not shown), suggesting that BCMA-mediated NF-κB activation is not due to non-specific activation of transcription and/or translation. Moreover, sTALL-1 stimulation potentiated BCMA-mediated NF-κB activation very well, especially when BCMA was expressed at low levels (FIG. 9). When BCMA was expressed at high levels, sTALL-1 stimulation could only weakly potentiate BCMA-mediated NF-κB activation. Two phenomena may account for this. First, it has been widely accepted that activation of TNF receptor family members is triggered by ligand-mediated oligomerization of the receptors. When the receptors are expressed at high levels, they may achieve maximum self-oligomerization even without their ligands. Secondly, at high expression levels of BCMA, downstream NF-κB activation signaling may be saturated. Taken together, these data suggest BCMA can activate NF-κB and that TALL-1 can signal through BCMA.

Example 6

The following example demonstrates that TRAF5, TRAF6, NIK, and IKKs are involved in BCMA-mediated NF-κB activation.

Previously, it had been shown that intracellular signaling proteins TRADD, TRAF2, TRAF5, TRAF6, RIP, NIK, IKKα, and IKKβ are involved in NF-κB activation pathways mediated by several TNF receptor family members (Nataga, (1997), Cell 88:355–365; Baker et al., (1998), Onocogene 17:3261–3270; Rothe et al., (1995), Science 269:1424–1427; Hu et al., (1999), J. Biol. Chem. 274:30603–30610). The present inventors examined whether these proteins are also involved in NF-κB activation by BCMA. Dominant negative mutants of TRADD, TRAF2, TRAF5, TRAF6, RIP, NIK, IKKα, and IKKβ were obtained for use in the assay as follows: TRADD(296S), Flag-TRAF2(87–501), Myc-RIP (559–671), Myc-NIK(KK/AA), Flag-IKKα(K44A), and Flag-IKKβ(K44A) were all provided by Dr. David Goeddel; Flag-TRAF6(289–523) was provided by Dr. Zhaodan Cao; and the mammalian expression plasmid for TRAF5 dominant negative mutant was constructed by insertion of a PCR product encoding amino acids 69–557 of human TRAF5 into the pRK-Flag vector(Hu et al., (1999), J. Biol. Chem. 274:30603–30610; Shu et al., (1997), Immunity 6:751–763). It is noted that details regarding the construction of the above-identified constructs provided by Dr. Goeddel or Dr. Cao are published as follows: TRADD (296S): (Park et al., 1996, J. Biol. Chem. 271, 9858–9862; Flag-TRAF2(87–501): Rothe et al., 1995, Science 269, 1424–1427; Myc-RIP(559–671): Hsu et al., 1996b, Immunity 4, 387–396; Myc-NIK(KK/AA): Song et al., 1997, Proc. Natl. Acad. Sci. U.S.A. 94, 9792–9796; Flag-IKKα: Regnier et al., 1997, Cell 90,373–383; Flag-IKKβ: Woronicz et al., 1997, Science 278,866–869; and, Flag-TRAF6 (289–523): Cao et al., 1996, Nature 383, 443–446. Each of the above-identified publications is incorporated in its entirety by reference.

Figure 10A:
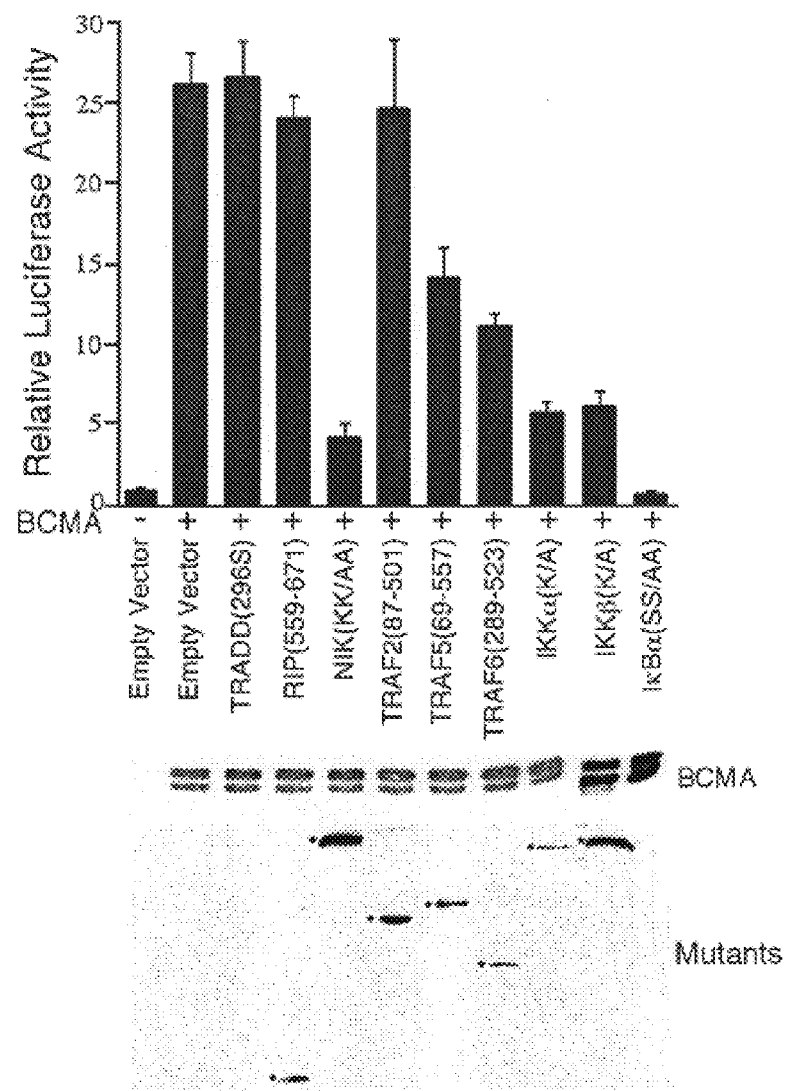
FIG. 10A is a bar graph and digitized image showing the effects of various dominant negative mutants on BCMA-mediated NF-κB activation.

In the first portion of the experiment (See FIG. 10A), 293 cells were transfected with 0.5 μg of NF-κB reporter plasmid (described in Example 4), 0.5 μg of BCMA-HA expression plasmid (described in Example 2), and 1 μg of control plasmid or expression plasmids for the dominant negative mutants indicated in FIG. 10A. 0.5 μg of crmA plasmid was also added to the Myc-RIP(559–671) transfections for inhibiting apoptosis. 20 hours after transfection, luciferase assays were performed as described in Example 4, and data were treated as described in Example 4. Expression of the HA-tagged BCMA and the Flag- or Myc-tagged mutants were examined by Western blots with antibodies against the HA, Flag, or Myc epitopes, respectively. TRADD(296S) and IκBα(SS/AA) (a mammalian expression plasmid for mutated Inhibitory κB, having amino acids S32 and S36 mutated to A32 and A36) are not tagged and could not be detected in the Western blot portion of the experiment (FIG. 10A, lower section). As shown in FIG. 10A (upper and lower sections), dominant negative mutants of TRAF5, TRAF6, NIK, IKKα and IKKβ, but not of TRADD, TRAF2, and RIP, inhibited BCMA-mediated NF-κB activation.

Figure 10B:
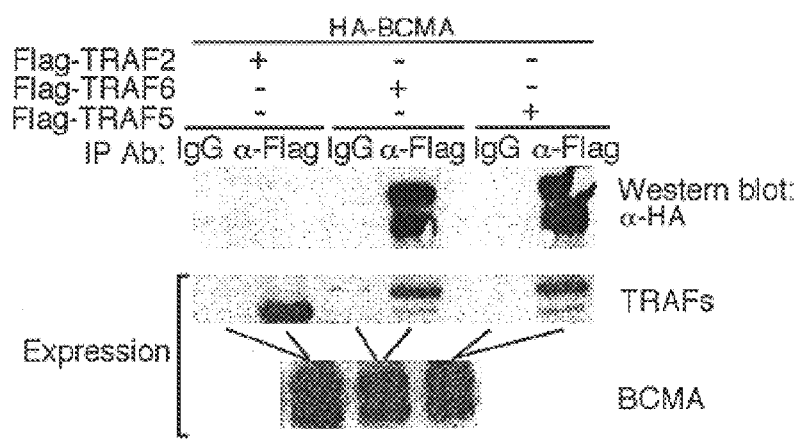
FIG. 10B is a digitized image of a western blot showing that BCMA interacts with TRAF5 and TRAF6 but not TRAF2.

In the second portion of the experiment (See FIG. 10B), 293 cells were transfected with expression plasmids for HA-BCMA and the plasmids indicated in FIG. 10B. Transfected cell lysates were immunoprecipitated with anti-Flag antibody or control IgG. The immunoprecipitates were analyzed by Western blot with anti-HA antibody (FIG. 10B; upper panel). Expression of the transfected proteins were detected by Western blots with anti-Flag (FIG. 10B; middle panel) or anti-HA antibody (FIG. 10B; lower panel). Consistent with the results demonstrated in FIG. 10A, the present inventors found that BCMA physically interacted with TRAF5 and TRAF6, but not TRAF2, TRADD or RIP in these co-immunoprecipitation experiments (FIG. 10B).

Taken together, these data suggest that TRAF5, TRAF6, NIK, IKKα and IKKβ, but not TRAF2, TRADD and RIP, are involved in BCMA-mediated NF-κB activation pathways. In conclusion, the data in Examples 2–5 suggest that BCMA is a B lymphocyte specific receptor for TALL-1 and that BCMA activates NF-κB through pathways involved in TRAF5, TRAF6, NIK, IKKα and IKKβ. The constitutive expression of TALL-1 by monocytes/macrophages and the specific expression of its receptor BCMA by B lymphocytes indicates that peripheral B lymphocyte proliferation, survival and activation are critically regulated by monocytes and related cells through secretion of sTALL-1. Manipulation of the TALL-1/BCMA signaling system is expected to provide novel approaches for modulation of B cell-mediated immune responses and diseases.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated TALL-1 receptor homologue, wherein said homologue comprises an amino acid sequence that is:
   a. at least about 60% identical to SEQ ID NO:11; and,
   b. less than 100% identical to an amino acid sequence selected from the group consisting of SEQ ID NO:11 and SEQ ID NO:17;
wherein said TALL-1 receptor homologue binds to TALL-1.

2. The isolated TALL-1 receptor homologue of claim 1, wherein said homologue is at least about 65% identical to SEQ ID NO:11.

3. The isolated TALL-1 receptor homologue of claim 1, wherein said homologue is at least about 75% identical to SEQ ID NO:11.

4. The isolated TALL-1 receptor homologue of claim 1, wherein said homologue is at least about 90% identical to SEQ ID NO:11.

5. The isolated TALL-1 receptor homologue of claim 1, wherein said homologue is less than about 95% identical to said amino acid sequence selected from the group consisting of SEQ ID NO:11 and SEQ ID NO:17.

6. The isolated TALL-1 receptor homologue of claim 1, wherein said homologue is less than about 90% identical to said amino acid sequence selected from the group consisting of SEQ ID NO:11 and SEQ ID NO:17.

7. The isolated TALL-1 receptor homologue of claim 1, wherein said homologue is a soluble TALL-1 receptor.

8. The isolated TALL-1 receptor homologue of claim 1, wherein said homologue activates NF-κB in a cell expressing said homologue through a TRAF5, TRAF6, NIK, IKKα and IKKβ dependent pathway.

9. The isolated TALL-1 receptor homologue of claim 1, wherein said homologue costimulates B lymphocyte proliferation in a B lymphocyte expressing said homologue.

10. A composition comprising:
   a. an isolated TALL-1 receptor homologue comprising an amino acid sequence selected that is:
      i. at least about 60% identical to SEQ ID NO:11; and
      ii. less than 100% identical to an amino acid sequence selected from the group consisting of SEQ ID NO:11 and SEQ ID NO:17;
   wherein said TALL-1 receptor homologue binds to TALL-1; and,
   b. a pharmaceutically acceptable carrier.

11. The composition of claim 10, wherein said isolated TALL-1 receptor homologue is a soluble TALL-1 receptor.

12. The composition of claim 10, wherein said isolated TALL-1 receptor homologue comprises an amino acid sequence that is at least about 65% identical to SEQ ID NO:11.

13. The composition of claim 10, wherein said TALL-1 receptor homologue comprises an amino acid sequence that is at least about 70% identical to SEQ ID NO:11.

14. The composition of claim 10, wherein said TALL-1 receptor homologue comprises an amino acid sequence that is at least about 80% identical to SEQ ID NO:11.

15. The composition of claim 10, wherein said TALL-1 receptor homologue comprises an amino acid sequence that is at least about 90% identical to SEQ ID NO:11.

16. The composition of claim 10, wherein said TALL-1 receptor homologue is less than about 95% identical to said amino acid sequence selected from the group consisting of SEQ ID NO:11 and SEQ ID NO:17.

17. The composition of claim 10, wherein said TALL-1 receptor homologue is less than about 90% identical to said amino acid sequence selected from the group consisting of SEQ ID NO:11 and SEQ ID NO:17.

18. An isolated TALL-1 receptor homologue, wherein said homologue comprises an amino acid sequence that is:
   a. at least about 60% identical to SEQ ID NO:11; and,
   b. less than 100% identical to an amino acid sequence selected from the group consisting of SEQ ID NO:11 and SEQ ID NO:17;
wherein said TALL-1 receptor homologue activates NF-κB in a cell expressing said homologue through a TRAF5, TRAF6, NIK, IKKα and IKKβ dependent pathway.

19. An isolated TALL-1 receptor homologue, wherein said homologue comprises an amino acid sequence that is:
   a. at least about 60% identical to SEQ ID NO:11; and,
   b. less than 100% identical to an amino acid sequence selected from the group consisting of SEQ ID NO:11 and SEQ ID NO:17;
wherein said TALL-1 receptor homologue costimulates B lymphocyte proliferation in a B lymphocyte expressing said homologue.

* * * * *